(12) United States Patent
Maahs et al.

(10) Patent No.: US 8,740,940 B2
(45) Date of Patent: *Jun. 3, 2014

(54) COMPRESSIBLE TISSUE ANCHOR ASSEMBLIES

(71) Applicants: Tracy D. Maahs, Yorba Linda, CA (US); Marvin C. Elmer, Rancho Santa Margarita, CA (US); Richard C. Ewers, Fullerton, CA (US)

(72) Inventors: Tracy D. Maahs, Yorba Linda, CA (US); Marvin C. Elmer, Rancho Santa Margarita, CA (US); Richard C. Ewers, Fullerton, CA (US)

(73) Assignee: USGI Medical, Inc., San Clemente, CA (US)

(*) Notice: Subject to any disclaimer, the term of this patent is extended or adjusted under 35 U.S.C. 154(b) by 52 days.

This patent is subject to a terminal disclaimer.

(21) Appl. No.: 13/748,302

(22) Filed: Jan. 23, 2013

(65) Prior Publication Data

US 2013/0138151 A1    May 30, 2013

Related U.S. Application Data

(63) Continuation of application No. 12/724,348, filed on Mar. 15, 2010, now Pat. No. 8,382,800, which is a continuation of application No. 11/404,423, filed on Apr. 14, 2006, now Pat. No. 7,678,135, which is a continuation-in-part of application No. 11/179,082, filed on Jul. 11, 2005, now Pat. No. 7,736,379, which is a continuation-in-part of application No. 10/865,243, filed on Jun. 9, 2004, now Pat. No. 8,206,417.

(51) Int. Cl.
    *A61B 17/04* (2006.01)

(52) U.S. Cl.
    USPC .......................................... 606/232

(58) Field of Classification Search
    USPC ......... 606/198, 191, 213, 215, 216, 200, 218, 606/221, 232, 233
    See application file for complete search history.

(56) References Cited

U.S. PATENT DOCUMENTS

| | | |
|---|---|---|
| 2,201,610 A | 5/1940 | Dawson, Jr. |
| 2,413,142 A | 12/1945 | Jones et al. |
| 3,150,379 A | 9/1964 | Brown |
| 3,166,072 A | 1/1965 | Sullivan, Jr. |
| 3,494,006 A | 2/1970 | Brumlik |
| 3,646,615 A | 3/1972 | Ness |
| 3,664,345 A | 5/1972 | Dabbs et al. |
| 3,753,438 A | 8/1973 | Wood et al. |
| 3,867,944 A | 2/1975 | Samuels |
| 3,874,388 A | 4/1975 | King et al. |
| 3,910,281 A | 10/1975 | Kletschka et al. |
| 3,976,079 A | 8/1976 | Samuels et al. |

(Continued)

FOREIGN PATENT DOCUMENTS

| | | |
|---|---|---|
| EP | 0847727 A1 | 6/1998 |
| EP | 1031321 A1 | 8/2000 |

(Continued)

*Primary Examiner* — Katherine Dowe
*Assistant Examiner* — Michael Mendoza
(74) *Attorney, Agent, or Firm* — Kenneth H. Ohriner; Perkins Coie LLP

(57) ABSTRACT

Apparatus and methods optimize anchoring force in securing tissue folds. Over-compression of the tissue directly underlying the anchors is avoided by utilizing tissue anchors having expandable designs configured to minimize contact area between the anchor and tissue. When the anchor is in its expanded configuration, a load is applied to the anchor until it is optimally configured to accommodate a range of deflections while the anchor itself exerts a substantially constant force against the tissue.

19 Claims, 23 Drawing Sheets

(56) References Cited

U.S. PATENT DOCUMENTS

| | | |
|---|---|---|
| 4,007,743 A | 2/1977 | Blake |
| 4,060,089 A | 11/1977 | Noiles |
| 4,069,825 A | 1/1978 | Akiyama |
| 4,235,238 A | 11/1980 | Ogiu et al. |
| 4,367,746 A | 1/1983 | Derechinsky |
| 4,414,720 A | 11/1983 | Crooms |
| 4,462,402 A | 7/1984 | Burgio et al. |
| 4,494,531 A | 1/1985 | Gianturco |
| 4,532,926 A | 8/1985 | O'Holla |
| 4,534,350 A | 8/1985 | Golden et al. |
| 4,548,202 A | 10/1985 | Duncan |
| 4,586,503 A | 5/1986 | Kirsch et al. |
| 4,592,339 A | 6/1986 | Kuzmak et al. |
| 4,592,356 A | 6/1986 | Gutierrez |
| 4,595,007 A | 6/1986 | Mericle |
| 4,610,250 A | 9/1986 | Green |
| 4,669,473 A | 6/1987 | Richards et al. |
| 4,705,040 A | 11/1987 | Mueller et al. |
| 4,711,002 A | 12/1987 | Kreeger |
| 4,724,840 A | 2/1988 | McVay et al. |
| 4,750,492 A | 6/1988 | Jacobs |
| 4,765,335 A | 8/1988 | Schmidt et al. |
| 4,832,055 A | 5/1989 | Palestrant |
| 4,841,888 A | 6/1989 | Mills et al. |
| 4,873,976 A | 10/1989 | Schreiber |
| 4,890,615 A | 1/1990 | Caspari et al. |
| 4,923,461 A | 5/1990 | Caspari et al. |
| 4,929,240 A | 5/1990 | Kirsch et al. |
| 4,957,498 A | 9/1990 | Caspari et al. |
| 5,032,127 A | 7/1991 | Frazee et al. |
| 5,035,692 A | 7/1991 | Lyon et al. |
| 5,041,129 A | 8/1991 | Hayhurst et al. |
| 5,059,201 A | 10/1991 | Asnis |
| 5,100,418 A | 3/1992 | Yoon et al. |
| 5,108,420 A | 4/1992 | Marks |
| 5,122,136 A | 6/1992 | Guglielmi et al. |
| 5,123,914 A | 6/1992 | Cope |
| 5,176,691 A | 1/1993 | Pierce |
| 5,201,746 A | 4/1993 | Shichman |
| 5,203,864 A | 4/1993 | Phillips |
| 5,217,471 A | 6/1993 | Burkhart |
| 5,217,473 A | 6/1993 | Yoon |
| 5,222,508 A | 6/1993 | Contarini |
| 5,222,961 A | 6/1993 | Nakao et al. |
| 5,224,946 A | 7/1993 | Hayhurst et al. |
| 5,234,430 A | 8/1993 | Huebner |
| 5,234,445 A | 8/1993 | Walker et al. |
| 5,250,053 A | 10/1993 | Snyder |
| 5,261,916 A | 11/1993 | Engelson |
| 5,268,001 A | 12/1993 | Nicholson et al. |
| 5,282,827 A | 2/1994 | Kensey et al. |
| 5,284,488 A | 2/1994 | Sideris |
| 5,304,184 A | 4/1994 | Hathaway et al. |
| 5,304,195 A | 4/1994 | Twyford, Jr. et al. |
| 5,304,204 A | 4/1994 | Bregen |
| 5,316,543 A | 5/1994 | Eberbach |
| 5,330,503 A | 7/1994 | Yoon |
| 5,334,217 A | 8/1994 | Das |
| 5,342,376 A | 8/1994 | Ruff |
| 5,354,298 A | 10/1994 | Lee et al. |
| 5,366,459 A | 11/1994 | Yoon |
| 5,366,479 A | 11/1994 | McGarry et al. |
| 5,372,146 A | 12/1994 | Branch |
| 5,372,604 A | 12/1994 | Trott |
| 5,374,275 A | 12/1994 | Bradley et al. |
| 5,380,334 A | 1/1995 | Torrie et al. |
| 5,403,329 A | 4/1995 | Hinchcliffe |
| 5,417,691 A | 5/1995 | Hayhurst |
| 5,417,699 A | 5/1995 | Klein et al. |
| 5,425,744 A | 6/1995 | Fagan et al. |
| 5,429,598 A | 7/1995 | Waxman et al. |
| 5,431,666 A | 7/1995 | Sauer et al. |
| 5,433,727 A | 7/1995 | Sideris |
| 5,437,680 A | 8/1995 | Yoon |
| 5,437,681 A | 8/1995 | Meade et al. |
| 5,445,167 A | 8/1995 | Yoon et al. |
| 5,458,609 A | 10/1995 | Gordon et al. |
| 5,462,560 A | 10/1995 | Stevens |
| 5,462,561 A | 10/1995 | Voda |
| 5,470,337 A | 11/1995 | Moss |
| 5,470,338 A | 11/1995 | Whitfield et al. |
| 5,476,470 A | 12/1995 | Fitzgibbons, Jr. |
| 5,478,354 A | 12/1995 | Tovey et al. |
| 5,480,405 A | 1/1996 | Yoon |
| 5,496,332 A | 3/1996 | Sierra et al. |
| 5,496,334 A | 3/1996 | Klundt et al. |
| 5,499,991 A | 3/1996 | Garman et al. |
| 5,501,691 A | 3/1996 | Goldrath |
| 5,507,811 A | 4/1996 | Koike et al. |
| 5,520,691 A | 5/1996 | Branch |
| 5,520,701 A | 5/1996 | Lerch |
| 5,522,843 A | 6/1996 | Zang |
| 5,527,321 A | 6/1996 | Hinchliffe |
| 5,527,322 A | 6/1996 | Klein et al. |
| 5,527,342 A | 6/1996 | Pietrzak et al. |
| 5,531,759 A | 7/1996 | Kensey et al. |
| 5,531,788 A | 7/1996 | Dibie et al. |
| 5,540,704 A | 7/1996 | Gordon et al. |
| 5,549,618 A | 8/1996 | Fleenor et al. |
| 5,562,684 A | 10/1996 | Kammerer |
| 5,562,686 A | 10/1996 | Sauer et al. |
| 5,562,688 A | 10/1996 | Riza |
| 5,569,274 A | 10/1996 | Rapacki et al. |
| 5,569,306 A | 10/1996 | Thal |
| 5,571,119 A | 11/1996 | Atala |
| 5,573,540 A | 11/1996 | Yoon |
| 5,573,548 A | 11/1996 | Nazre et al. |
| 5,578,045 A | 11/1996 | Das |
| 5,582,616 A | 12/1996 | Bolduc et al. |
| 5,584,835 A | 12/1996 | Greenfield |
| 5,584,859 A | 12/1996 | Brotz |
| 5,601,557 A | 2/1997 | Hayhurst |
| 5,603,718 A | 2/1997 | Xu |
| 5,613,974 A | 3/1997 | Andreas et al. |
| 5,613,975 A | 3/1997 | Christy |
| 5,626,614 A | 5/1997 | Hart |
| 5,630,540 A | 5/1997 | Blewett |
| 5,632,752 A | 5/1997 | Buelna |
| 5,643,274 A | 7/1997 | Sander et al. |
| 5,643,295 A | 7/1997 | Yoon |
| 5,643,317 A | 7/1997 | Pavcnik et al. |
| 5,643,320 A | 7/1997 | Lower et al. |
| 5,658,312 A | 8/1997 | Green et al. |
| 5,658,313 A | 8/1997 | Thal |
| 5,662,662 A | 9/1997 | Bishop et al. |
| 5,662,663 A | 9/1997 | Shallman |
| 5,665,109 A | 9/1997 | Yoon |
| 5,665,112 A | 9/1997 | Thal |
| 5,667,513 A | 9/1997 | Torrie et al. |
| 5,679,005 A | 10/1997 | Einstein |
| 5,683,417 A | 11/1997 | Cooper |
| 5,683,419 A | 11/1997 | Thal |
| 5,690,655 A | 11/1997 | Hart et al. |
| 5,693,060 A | 12/1997 | Martin |
| 5,700,273 A | 12/1997 | Buelna et al. |
| 5,702,421 A | 12/1997 | Schneidt |
| 5,707,394 A | 1/1998 | Miller et al. |
| 5,709,708 A | 1/1998 | Thal |
| 5,713,903 A | 2/1998 | Sander et al. |
| 5,720,765 A | 2/1998 | Thal |
| 5,724,978 A | 3/1998 | Tenhoff |
| 5,725,552 A | 3/1998 | Kotula et al. |
| 5,732,707 A | 3/1998 | Widder et al. |
| 5,741,297 A | 4/1998 | Simon |
| 5,746,752 A | 5/1998 | Burkhart |
| 5,746,755 A | 5/1998 | Wood et al. |
| 5,752,963 A | 5/1998 | Allard et al. |
| 5,766,189 A | 6/1998 | Matsuno |
| 5,776,150 A | 7/1998 | Nolan et al. |
| 5,779,719 A | 7/1998 | Klein et al. |
| 5,782,865 A | 7/1998 | Grotz |
| 5,792,152 A | 8/1998 | Klein et al. |
| 5,797,929 A | 8/1998 | Andreas et al. |
| 5,797,960 A | 8/1998 | Stevens et al. |

(56) References Cited

U.S. PATENT DOCUMENTS

| | | |
|---|---|---|
| 5,810,849 A | 9/1998 | Kontos |
| 5,810,851 A | 9/1998 | Yoon |
| 5,810,853 A | 9/1998 | Yoon |
| 5,814,070 A | 9/1998 | Borzone et al. |
| 5,817,107 A | 10/1998 | Schaller |
| 5,817,110 A | 10/1998 | Kronner |
| 5,823,956 A | 10/1998 | Roth et al. |
| 5,824,011 A | 10/1998 | Stone et al. |
| 5,827,298 A | 10/1998 | Hart et al. |
| 5,829,447 A | 11/1998 | Stevens et al. |
| 5,836,955 A | 11/1998 | Buelna et al. |
| 5,840,078 A | 11/1998 | Yerys |
| 5,843,084 A | 12/1998 | Hart et al. |
| 5,843,126 A | 12/1998 | Jameel |
| 5,846,261 A | 12/1998 | Kotula et al. |
| 5,855,614 A | 1/1999 | Stevens et al. |
| 5,860,991 A | 1/1999 | Klein et al. |
| 5,861,003 A | 1/1999 | Latson et al. |
| 5,868,762 A | 2/1999 | Cragg et al. |
| 5,879,371 A | 3/1999 | Gardiner et al. |
| 5,888,247 A | 3/1999 | Benetti |
| 5,891,168 A | 4/1999 | Thal |
| 5,893,856 A | 4/1999 | Jacob et al. |
| 5,895,404 A | 4/1999 | Ruiz |
| 5,899,920 A | 5/1999 | DeSatnick et al. |
| 5,899,921 A | 5/1999 | Caspari et al. |
| 5,916,224 A | 6/1999 | Esplin |
| 5,925,059 A | 7/1999 | Palermo et al. |
| 5,928,260 A | 7/1999 | Chin et al. |
| 5,928,264 A | 7/1999 | Sugarbaker et al. |
| 5,944,738 A | 8/1999 | Amplatz et al. |
| 5,947,997 A | 9/1999 | Pavcnik et al. |
| 5,948,001 A | 9/1999 | Larsen |
| 5,954,732 A | 9/1999 | Hart et al. |
| 5,961,440 A | 10/1999 | Schwelch, Jr. et al. |
| 5,964,765 A | 10/1999 | Fenton, Jr. et al. |
| 5,964,783 A | 10/1999 | Grafton et al. |
| 5,976,127 A | 11/1999 | Lax |
| 5,976,158 A | 11/1999 | Adams et al. |
| 5,976,159 A | 11/1999 | Bolduc et al. |
| 5,980,558 A | 11/1999 | Wiley |
| 5,984,933 A | 11/1999 | Yoon |
| 5,993,476 A | 11/1999 | Groiso |
| 6,013,083 A | 1/2000 | Bennett |
| 6,027,523 A | 2/2000 | Schmieding |
| 6,033,430 A | 3/2000 | Bonutti |
| 6,036,699 A | 3/2000 | Andreas et al. |
| 6,045,497 A | 4/2000 | Schweich, Jr. et al. |
| 6,045,573 A | 4/2000 | Wenstrom, Jr. et al. |
| 6,050,936 A | 4/2000 | Schweich, Jr. et al. |
| 6,053,935 A | 4/2000 | Brenneman et al. |
| 6,059,715 A | 5/2000 | Schweich, Jr. et al. |
| 6,074,401 A | 6/2000 | Gardiner et al. |
| 6,077,214 A | 6/2000 | Mortier et al. |
| 6,077,281 A | 6/2000 | Das |
| 6,077,291 A | 6/2000 | Das |
| 6,079,414 A | 6/2000 | Roth |
| 6,110,183 A | 8/2000 | Cope |
| 6,113,609 A | 9/2000 | Adams |
| 6,113,611 A | 9/2000 | Allen et al. |
| 6,149,658 A | 11/2000 | Gardiner et al. |
| 6,152,935 A | 11/2000 | Kammerer et al. |
| 6,162,168 A | 12/2000 | Schweich, Jr. et al. |
| 6,165,119 A | 12/2000 | Schweich, Jr. et al. |
| 6,165,120 A | 12/2000 | Schweich, Jr. et al. |
| 6,167,889 B1 | 1/2001 | Benetti |
| 6,171,320 B1 | 1/2001 | Monassevitch |
| 6,174,323 B1 | 1/2001 | Biggs et al. |
| 6,183,411 B1 | 2/2001 | Mortier et al. |
| 6,214,007 B1 | 4/2001 | Anderson |
| 6,231,561 B1 | 5/2001 | Frazier et al. |
| 6,245,079 B1 | 6/2001 | Nobles et al. |
| 6,260,552 B1 | 7/2001 | Mortier et al. |
| 6,261,222 B1 | 7/2001 | Schweich, Jr. et al. |
| 6,264,602 B1 | 7/2001 | Mortier et al. |
| 6,270,515 B1 | 8/2001 | Linden et al. |
| 6,283,973 B1 | 9/2001 | Hubbard et al. |
| 6,290,674 B1 | 9/2001 | Roue et al. |
| 6,293,956 B1 | 9/2001 | Crainich et al. |
| 6,296,656 B1 | 10/2001 | Bolduc et al. |
| 6,306,159 B1 | 10/2001 | Schwartz et al. |
| 6,312,437 B1 | 11/2001 | Kortenbach |
| 6,315,789 B1 | 11/2001 | Cragg |
| 6,322,563 B1 | 11/2001 | Cummings et al. |
| 6,322,580 B1 | 11/2001 | Kanner |
| 6,332,468 B1 | 12/2001 | Benetti |
| 6,332,863 B1 | 12/2001 | Schweich, Jr. et al. |
| 6,332,864 B1 | 12/2001 | Schweich, Jr. et al. |
| 6,332,893 B1 | 12/2001 | Mortier et al. |
| 6,336,940 B1 | 1/2002 | Graf et al. |
| 6,346,074 B1 | 2/2002 | Roth |
| 6,348,064 B1 | 2/2002 | Kanner |
| 6,355,052 B1 | 3/2002 | Neuss et al. |
| 6,363,938 B2 | 4/2002 | Saadat et al. |
| 6,368,338 B1 | 4/2002 | Konya et al. |
| 6,368,339 B1 | 4/2002 | Amplatz |
| 6,375,668 B1 | 4/2002 | Gifford et al. |
| 6,387,104 B1 | 5/2002 | Pugsley, Jr. et al. |
| 6,402,679 B1 | 6/2002 | Mortier et al. |
| 6,402,680 B2 | 6/2002 | Mortier et al. |
| 6,406,420 B1 | 6/2002 | McCarthy et al. |
| 6,423,087 B1 | 7/2002 | Sawada |
| 6,425,911 B1 | 7/2002 | Akerfeldt et al. |
| 6,447,533 B1 | 9/2002 | Adams |
| 6,589,208 B2 | 7/2003 | Ewers et al. |
| 6,592,596 B1 | 7/2003 | Geitz |
| 6,656,194 B1 | 12/2003 | Gannoe et al. |
| 6,736,828 B1 | 5/2004 | Adams et al. |
| 6,746,460 B2 | 6/2004 | Gannoe et al. |
| 2001/0016675 A1 | 8/2001 | Mortier et al. |
| 2001/0025171 A1 | 9/2001 | Mortier et al. |
| 2001/0051815 A1 | 12/2001 | Esplin |
| 2002/0010490 A1 | 1/2002 | Schaller et al. |
| 2002/0013608 A1 | 1/2002 | ElAttrache et al. |
| 2002/0019649 A1 | 2/2002 | Sikora et al. |
| 2002/0022851 A1 | 2/2002 | Kalloo et al. |
| 2002/0029080 A1 | 3/2002 | Mortier et al. |
| 2002/0049458 A1 | 4/2002 | Singhatat |
| 2002/0058855 A1 | 5/2002 | Schweich et al. |
| 2002/0068849 A1 | 6/2002 | Schweich et al. |
| 2002/0077524 A1 | 6/2002 | Schweich et al. |
| 2002/0082621 A1 | 6/2002 | Schurr et al. |
| 2002/0082622 A1 | 6/2002 | Kane |
| 2002/0107530 A1 | 8/2002 | Sauer et al. |
| 2002/0116012 A1 | 8/2002 | May et al. |
| 2002/0183768 A1 | 12/2002 | Deem et al. |
| 2003/0109900 A1 | 6/2003 | Martinek |
| 2003/0158582 A1 | 8/2003 | Bonutti et al. |
| 2003/0167062 A1 | 9/2003 | Gambale et al. |
| 2004/0030347 A1 | 2/2004 | Gannoe et al. |
| 2004/0088008 A1 | 5/2004 | Gannoe et al. |
| 2004/0093091 A1 | 5/2004 | Gannoe et al. |
| 2004/0122456 A1 | 6/2004 | Saadat et al. |
| 2004/0122474 A1 | 6/2004 | Gellman et al. |
| 2004/0162568 A1 | 8/2004 | Saadat et al. |
| 2004/0176784 A1 | 9/2004 | Okada |
| 2005/0149115 A1 | 7/2005 | Roue et al. |
| 2005/0251157 A1 | 11/2005 | Saadat et al. |
| 2005/0251205 A1 | 11/2005 | Ewers et al. |
| 2005/0251206 A1 | 11/2005 | Maahs et al. |
| 2005/0251207 A1 | 11/2005 | Flores et al. |
| 2005/0273135 A1 | 12/2005 | Chanduszko et al. |
| 2005/0277966 A1 | 12/2005 | Ewers et al. |
| 2005/0277981 A1 | 12/2005 | Maahs et al. |
| 2006/0217762 A1 | 9/2006 | Maahs et al. |

FOREIGN PATENT DOCUMENTS

| | | |
|---|---|---|
| WO | WO 9519140 | 7/1995 |
| WO | WO 00/40159 | 7/2000 |
| WO | WO 00/57796 | 10/2000 |
| WO | WO 01/21246 | 3/2001 |
| WO | WO 01/66001 | 9/2001 |
| WO | WO 01/85034 | 11/2001 |

(56) References Cited

FOREIGN PATENT DOCUMENTS

| WO | WO 01/89392 | 11/2001 |
|---|---|---|
| WO | WO 02/00119 | 1/2002 |
| WO | WO 02/064012 | 8/2002 |
| WO | WO 02/085252 | 10/2002 |
| WO | WO 02/094105 | 11/2002 |
| WO | WO 03/007799 | 1/2003 |
| WO | WO 2004/019787 | 3/2004 |
| WO | WO 2004/019788 | 3/2004 |
| WO | WO 2004/056273 | 7/2004 |
| WO | WO 2004/075787 | 9/2004 |

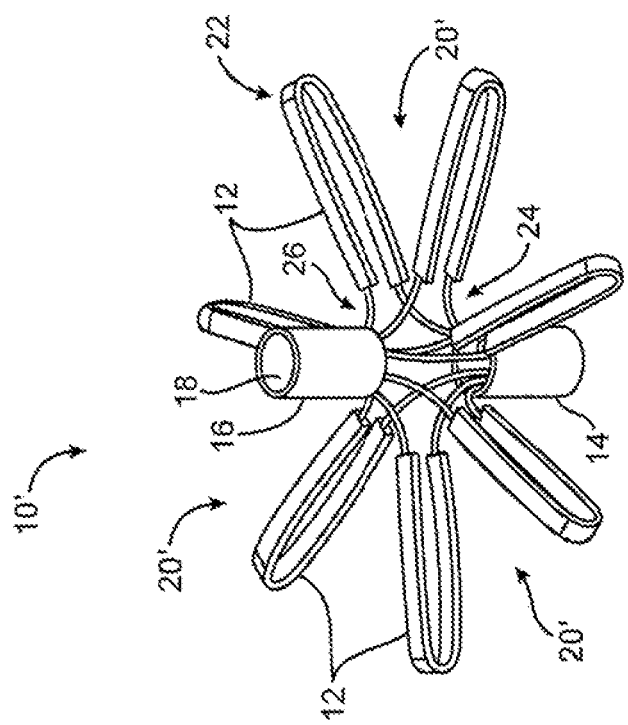
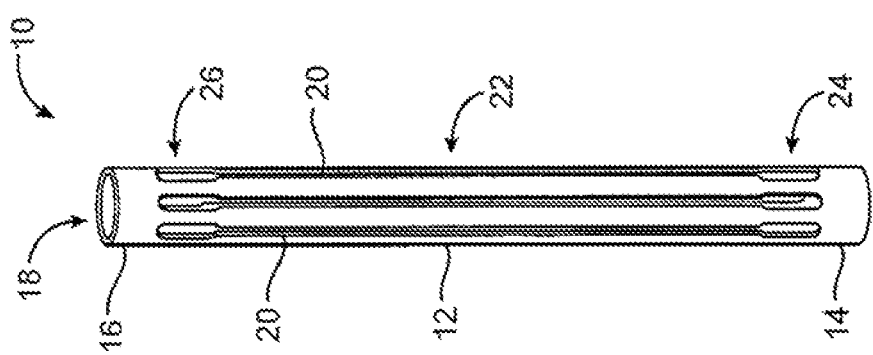

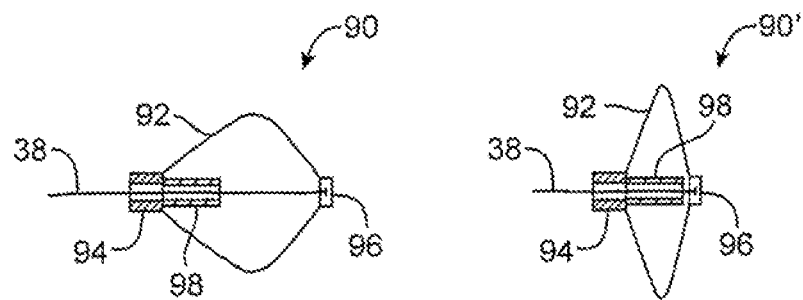
FIG. 6A  FIG. 6B
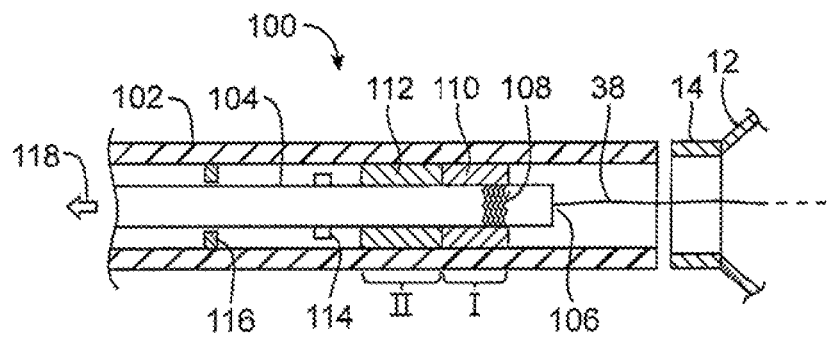
FIG. 7A
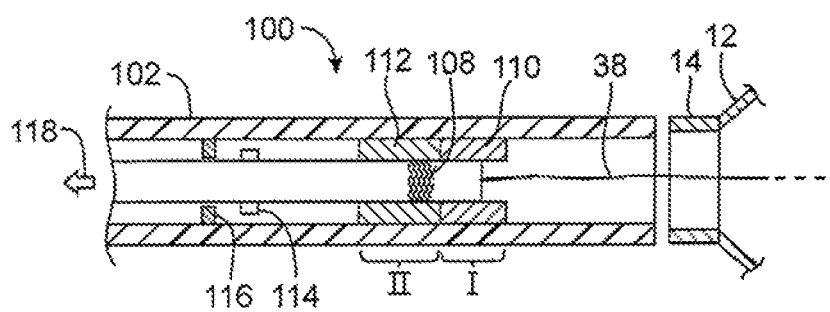
FIG. 7B
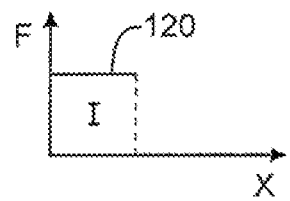 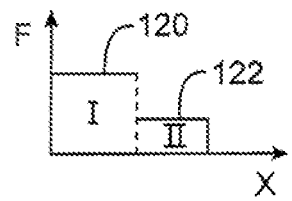
FIG. 8A  FIG. 8B

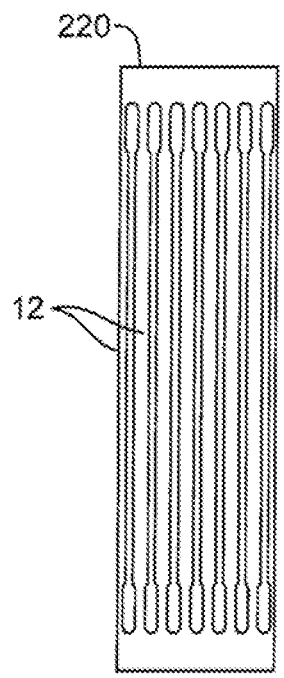
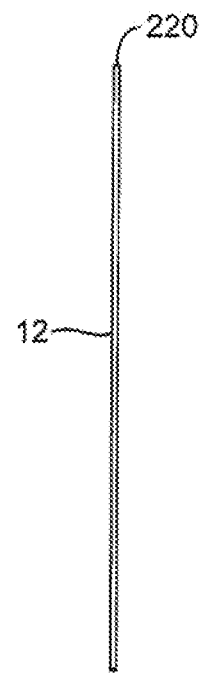
FIG. 15A  FIG. 15B
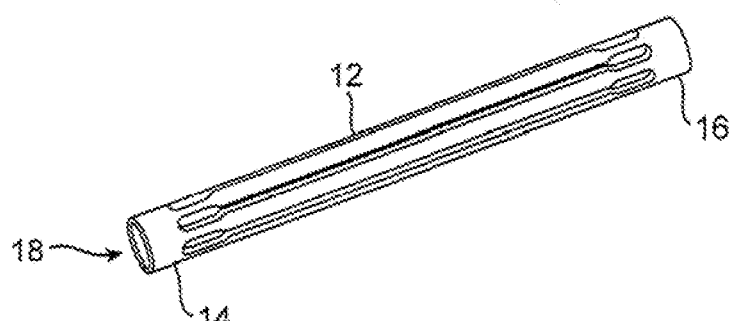
FIG. 15C

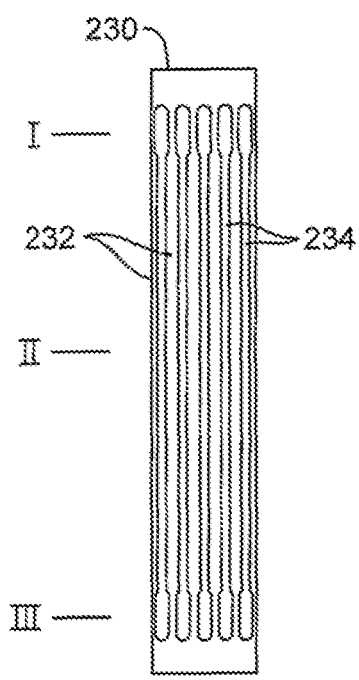 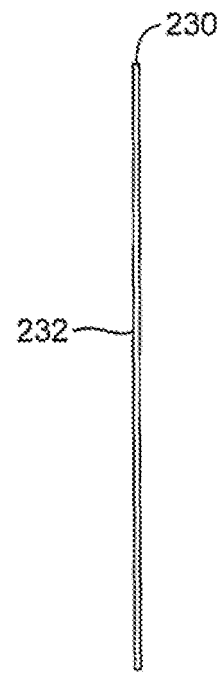
FIG. 16A  FIG. 16B
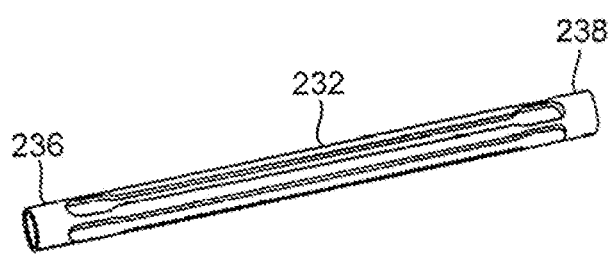
FIG. 16C

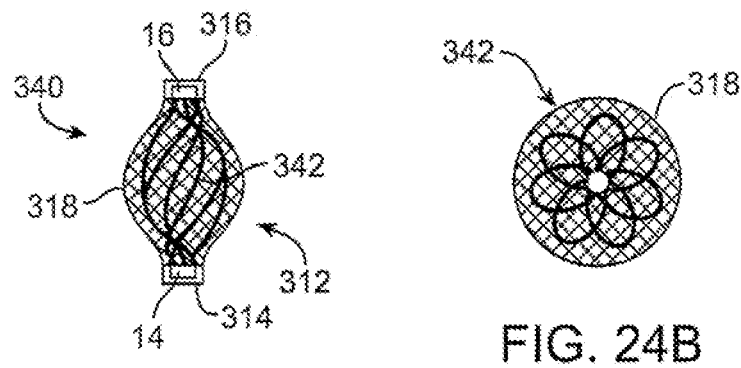
FIG. 24A
FIG. 24B
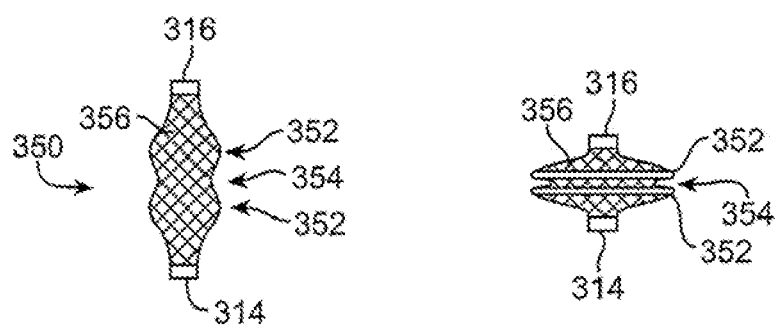
FIG. 25A
FIG. 25B
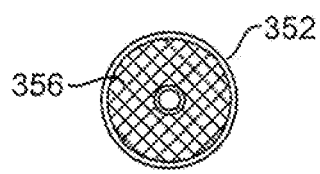
FIG. 25C

COMPRESSIBLE TISSUE ANCHOR ASSEMBLIES

CROSS-REFERENCE TO RELATED APPLICATIONS

This application is a continuation of U.S. patent application Ser. No. 12/724,348, now U.S. Pat. No. 8,382,800 filed Mar. 15, 2010, and now pending, which is a continuation of U.S. patent application Ser. No. 11/404,423, now U.S. Pat. No. 7,678,135 filed Apr. 14, 2006, which is a continuation-in-part of U.S. patent application Ser. No. 11/179,082, now U.S. Pat. No. 7,736,379 filed Jul. 11, 2005, which is a continuation-in-part of U.S. patent application Ser. No. 10/865,243, now U.S. Pat. No. 8,206,417 filed Jun. 9, 2004, each of which is incorporated herein by reference in its entirety.

FIELD OF THE INVENTION

The present invention relates to improved tissue anchors for securement against tissue. More particularly, the present invention relates to tissue anchors which are deployable into or against tissue for securing portions thereof.

BACKGROUND OF THE INVENTION

Morbid obesity is a serious medical condition pervasive in the United States and other countries, its complications include hypertension, diabetes, coronary artery disease, stroke, congestive heart failure, multiple orthopedic problems and pulmonary insufficiency with markedly decreased life expectancy.

A number of surgical techniques have been developed to treat morbid obesity, e.g., bypassing an absorptive surface of the small intestine, or reducing the stomach size. However, many conventional surgical procedures may present numerous life-threatening post-operative complications, and may cause atypical diarrhea, electrolytic imbalance, unpredictable weight loss and reflux of nutritious chyme proximal to the site of the anastomosis.

Furthermore, the sutures or staples that are often used in these surgical procedures typically require extensive training by the clinician to achieve competent use, and may concentrate significant force over a small surface area of the tissue, thereby potentially causing the suture or staple to tear through the tissue Moreover, the tissue underlying the suture or staple may be subject to becoming over-compressed to the point of becoming subject to necrosis. Many of the surgical procedures require regions of tissue within the body to be approximated towards one another and reliably secured without necrosing the approximated tissue. The gastrointestinal lumen includes four tissue layers, wherein the mucosa layer is the inner-most tissue layer followed by connective tissue, the muscularis layer and the serosa layer.

One problem with conventional gastrointestinal reduction systems is that the anchors (or staples) should engage at least the muscularis tissue layer in order to provide a proper foundation. In other words, the mucosa and connective tissue layers typically are not strong enough to sustain the tensile loads imposed by normal movement of the stomach wail during ingestion and processing of food. In particular, these layers tend to stretch elastically rather than firmly hold the anchors (or staples) in position, and accordingly, the more rigid muscularis and/or serosa layer should ideally be engaged. This problem of capturing the muscularis or serosa layers becomes particularly acute where it is desired to place an anchor or other apparatus transesophageally rather than intraoperative, since care must be taken in piercing the tough stomach waif not to inadvertently puncture adjacent tissue or organs. Thus, an anchor is desirably non-traumatic to the surrounding tissue. Moreover, the anchor is also desirably strong enough to withstand the movement of the tissue.

One conventional method for securing anchors within a body lumen to the tissue is to utilize sewing devices to suture the stomach wall into folds. This procedure typically involves advancing a sewing instrument through the working channel of an endoscope and into the stomach and against the stomach wail tissue. The contacted tissue is then typically drawn into the sewing instrument where one or more sutures or tags are implanted to hold the suctioned tissue in a folded condition known as a plication. Another method involves manually creating sutures for securing the plication.

One of the problems associated with these types of procedures is the time and number of intubations needed to perform the various procedures endoscopically. Another problem is the time required to complete a plication from the surrounding tissue with the body lumen, in the period of time that a patient is anesthetized, procedures such as for the treatment of morbid obesity or for GERD must be performed to completion. Accordingly, the placement and securement of the tissue plication should ideally be relatively quick and performed with a minimal level of confidence.

Another problem with conventional methods involves ensuring that the staple, knotted suture, or clip is secured tightly against the tissue and that the newly created plication will not relax under any slack which may be created by slipping staples, knots, or clips. Other conventional tissue securement devices such as suture anchors, twist ties, crimps, etc. are also often used to prevent sutures from slipping through tissue. However, many of these types of devices are typically large and unsuitable for low-profile delivery through the body, e.g., transesophageally. Moreover, these methods do not allow the surgeon to gauge the amount of force being applied to or against the tissue by the sutures, staple, clip, etc. Thus, over-tightening of the tissue anchor against the underlying tissue surface may be problematic.

Moreover, when grasping or clamping onto or upon the layers of tissue with conventional anchors, sutures, staples, clips, etc., many of these devices are configured to be placed only after the tissue has been plicated and not during the actual plication procedure.

SUMMARY OF THE INVENTION

In securing the tissue folds or anchoring to or from these tissue folds or plications, over-compression of the issue directly underlying the tissue anchors is preferably avoided. Over-compression of the underlying tissue may occur if the anchor compresses the tissue to such a degree that tissue necrosis or cutting of the underlying muscularis or serosal tissue by the anchor occurs. Accordingly, a tissue anchor is preferably configured to maintain or secure a tissue plication yet still allow for adequate blood flow to occur within the tissue underlying the anchor. As such, the tissue anchor is preferably configured to accommodate a range of deflections due to various movements of the tissue due to, e.g., peristalsis, patient movement, weight of the gastrointestinal organ itself, etc., while maintaining or exerting a substantially constant force against the tissue.

A particular type of anchor which may be utilized is a reconfigurable "basket"-type anchor generally having a number of configurable struts or legs extending between at least two collars or bushing members. This anchor may have a low-profile delivery configuration and a radially expanded anchoring configuration. When expanded, each arm of the anchor may be separated from one another by a spacing or opening. The spacing is preferably created to minimize the contact area between the anchor body and the underlying tissue surface to allow for greater blood flow in the tissue and to inhibit necrosis of the tissue.

The anchor may be made from various materials, e.g., spring stainless steel, plastics such as polyurethane, nylon, etc., but is preferably made from a shape memory or superelastic alloy, e.g., Nitinol. The anchor may thus be shaped and heat-set such that it self-forms or automatically configures itself from the delivery configuration to the expanded configuration upon release of a constraining force, e.g., when the anchor is ejected from its delivery needle or catheter. Sutures may connect a proximal anchor to a distal anchor through the tissue fold to secure the plication.

When the anchor has been configured into its expanded configuration, a load or force may be applied to the anchor until the anchor has been optimally configured to accommodate a range of deflections while the anchor itself maintains or exerts a substantially constant force against the tissue. Anchor deflection may occur, e.g., when the proximal and distal collars of an anchor have been advanced or urged towards one another such that the arms or struts extending therebetween are at least partially deflected. Moreover, anchor deflection may be due to various movements of the tissue attributable to, e.g., peristalsis, patient movement, weight of the gastrointestinal organ itself, etc.

Knowing the anchor deflection-to-exerted force characteristics for a given anchor, one may load an anchor with a tension or compression force such that subsequent deflections of the underlying tissue being anchored occur within specified ranges, such as the optimal range. For instance, an anchor may be pre-loaded such that tissue fluctuations or movements occur within the optimal window or range where the force exerted by the anchor remains relatively constant over a range of deflections. This in turn may ensure that the under tying tissue is not subject to over-compression by the anchors.

One method for limiting the loading or pre-load force upon an anchor may involve including a post or stop in the anchor body which limits the proximal deflection of the distal collar and thus prevents over-compression of the anchor against the tissue. Another variation may utilize friction-producing regions within the anchor delivery catheter. As the anchor is tensioned, various regions may produce frictional forces which vary in accordance to the degree of anchor deflection. A change in the detected frictional force may thus be utilized to indicate that anchor has been configured within an optimal range of deflections.

Another variation may include the use of a spring member having a known spring constant or fuse-like member which are set to break or fail at predetermined levels of detected force to detect the amount of deflection an anchor has undergone. Alternatively, measurement of material deformation via strain gauges may also be utilized to determine the amount of deflection. The anchor tensioning assembly may thus be configured to indicate when the anchor has been deflected to a predetermined level, when the anchor has been deflected within the optimal range.

Yet another variation may include configuring the proximal collar of the anchor to prevent the passage of stop member contained within the anchor. Thus, the length of suture extending from the stop member to the attachment point within the anchor may be of a predetermined length such that when the stop member is seated against the proximal collar, the suture length may compress the anchor into a predetermined deflection level. This deflection level may be preset to configure the anchor to any desired configuration, as described above.

The anchors may be tensioned through various methods. One particular method may include tensioning the anchors via an elongate rigid or flexible shaft having a hollow lumen. A tensioning mechanism, which is configured to receive the anchors and grasp a tensioning suture, may be positioned near or at the distal end of the elongate shaft. After the anchor or anchors have been desirably tensioned, the shaft may simply be removed from the body.

Various other factors of the tissue anchors may be modified to affect the tensioning and loading characteristics when deflecting the anchors. Moreover, some of the factors may also affect the interaction of the anchor with respect to the tissue in ensuring that the tissue is not over-compressed and that adequate blood flow may occur within the tissue directly beneath the anchor. Some of the factors may include, e.g., varying the number of arms or struts of the anchor, positioning of the arms, configuration of the arms, the length of the collars, etc.

Moreover, exposed portions of the anchor may be optionally coated or covered with a material to protect against exposure to foreign materials, e.g., food or other object which may be ingested by the patient, other surgical tools, etc. Accordingly, a biocompatible coating or covering may be placed over the entire length of the anchor arms or only along the portions of the arms not against the tissue. Alternatively, a mesh or skirt-like covering may be placed over the exposed portion of the anchor or the entire anchor itself may be covered with a distensible or expandable covering or mesh.

In another variation, a separate mesh basket and basket anchor may be assembled as a hybrid combination where the basket anchor is placed within the mesh basket such that they are freely floating with respect to one another. Alternatively, one or both collared ends of both baskets, i.e., the basket anchor and mesh basket, may be formed or otherwise adhered to one another, in yet another variation, a mesh basket, alone or in combination with a basket anchor, may be pre-formed to compress into a ringed configuration which inhibits or resists being pulled through a tissue region when deployed and compressed against the tissue surface. In these and other variations, a biasing element such as a spring may also be utilized to connect the collars of the mesh anchor to one another. Use of a spring may facilitate at least the partial expansion of a mesh anchor when deployed or released from the deployment instrument and inhibit the anchors from being pulled through a tissue region.

BRIEF DESCRIPTION OF THE DRAWINGS

FIGS. 1A and 1B show perspective views of an example of a basket-type anchor in a delivery configuration and an expanded configuration, respectively.

FIGS. 6A and 6B show cross-sectional side views of an anchor having a center post extending within the anchor for limiting the compression of the anchor.

FIGS. 7A and 7B show cross-sectional side views of one variation of an anchor tensioning or loading mechanism utilizing different frictional coefficients to indicate the load placed upon the anchor.

FIGS. 8A and 8B show the corresponding frictional force generated utilizing the device of FIGS. 7A and 7B, respectively.

FIGS. 15A and 15B show side and edge views, respectively, of one variation of a basket anchor in a flattened and splayed view FIG. 15C shows a perspective view of the anchor of FIGS. 15A and 15B in its delivery configuration.

FIGS. 16A and 16B show side and edge views, respectively, of another variation of a basket anchor in a flattened and splayed view FIG. 16C shows a perspective view of the anchor of FIGS. 16A and 16B in its delivery configuration.

FIG. 24A illustrates a side view of another hybrid basket assembly having a mesh anchor with a basket anchor contained within having arm members or struts which are formed in a curved, spiraled, or arcuate shape between the collars.

FIG. 24B shows the basket assembly of FIG. 24A compressed into its disk-shaped configuration with curved or spiraled arm members compressed into a looped, spiraled, or flower-shaped configuration.

FIG. 25A illustrates a low-profile configuration of an anchor having one or more radially-biased bulges pre-formed between at least one inwardly-biased radius.

FIGS. 25B and 25C show the basket of FIG. 25A in compressed side and top views, respectively.

DETAILED DESCRIPTION OF THE INVENTION

Figure 2A:
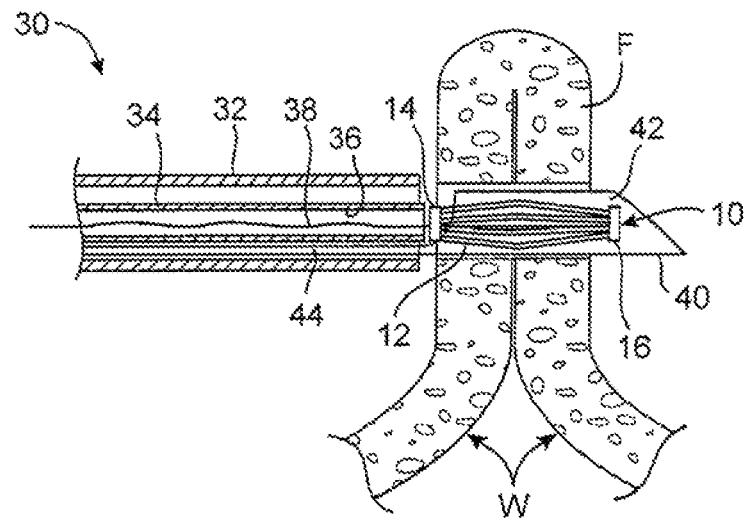
FIG. 2A shows a cross-sectional side view of one variation for delivering a basket anchor through a needle for anchoring to a fold of tissue.

Generally, in creating and securing a plication within a body lumen of a patient, various methods and devices may be implemented. The anchoring and securement devices may be delivered and positioned via an endoscopic apparatus that engages a tissue wall of the gastrointestinal lumen, creates one or more tissue folds, and disposes one or more of the anchors through the tissue fold(s).

In securing the tissue folds or anchoring to or from these tissue folds or plications, over-compression of the tissue directly underlying the tissue anchors is preferably avoided. Over-compression of the underlying tissue may occur if the anchor compresses the tissue to such a degree that tissue necrosis or cutting of the underlying muscularis or serosal tissue by the anchor occurs. The anchor preferably exerts a force, e.g., about 0.1-0.5 lbs, sufficient to maintain or secure a tissue plication yet still allows for adequate blood flow to occur within the tissue underlying the anchor. Accordingly, the tissue anchor is preferably configured to accommodate a range of deflections due to various movements of the tissue due to, e.g., peristalsis, patient movement, weight of the gastrointestinal organ itself, etc., while maintaining or exerting a substantially constant force against the tissue.

Formation of a tissue fold may be accomplished using at least two tissue contact areas that are separated by a linear or curvilinear distance, wherein the separation distance between the tissue contact points affects the length and/or depth of the fold. In operation, a tissue grabbing assembly engages or grasps the tissue wall in its normal state (i.e., non-folded and substantially flat), thus providing a first tissue contact area. The first tissue contact area then is moved to a position proximal of a second tissue contact area to form the tissue fold. The tissue anchor assembly then may be extended across the tissue fold at the second tissue contact area. Optionally, a third tissue contact point may be established such that, upon formation of the tissue fold, the second and third tissue contact areas are disposed on opposing sides of the tissue fold, thereby providing backside stabilization during extension of the anchor assembly across the tissue fold from the second tissue contact area.

The first tissue contact area may be utilized to engage and then stretch or rotate the tissue wall over the second tissue contact area to form the tissue fold. The tissue fold may then be articulated to a position where a portion of the tissue fold overlies the second tissue contact area at an orientation that is substantially normal to the tissue fold. A tissue anchor may then be delivered across the tissue fold at or near the second tissue contact area. One apparatus which is particularly suited to deliver the anchoring and securement devices described herein may be seen in further detail in co-pending U.S. patent application Ser. No. 10/735,030 filed Dec. 12, 2003, which is incorporated herein by reference in its entirety.

Various tissue anchors may be utilized for securing the tissue plications within the lumen. For instance, examples of tissue anchors which may be utilized are disclosed in co-pending U.S. patent application Ser. No. 10/612,170 filed Jul. 1, 2003, which is incorporated herein by reference in its entirety. Moreover, a single type of anchor may be used exclusively in an anchor assembly; alternatively, a combination of different anchor types may be used in an anchor assembly. One particular type of anchor described herein is a re-configurable "basket"-type anchor, which may generally comprise a number of configurable struts or legs extending between at least two collars or bushing members.

As described further below, an anchor may be adapted to exert a substantially constant force against a tissue surface, the anchor generally comprising a proximal collar, a distal collar, a plurality of deformable arms each extending between the proximal and distal collars, wherein the anchor is adapted to self-configure from a delivery configuration to an expanded configuration for placement against the tissue surface, and wherein the anchor is further adapted to exert a substantially constant force against the tissue surface over a range of deflections when the proximal and distal collars are moved relative to one another.

One particular illustrative basket anchor is shown in the perspective views of FIGS. 1A and 1B. FIG. 1A shows deformable basket anchor 10 in a low-profile delivery configuration having proximal collar or bushing 14 and distal collar or bushing 16 with a plurality of struts or arms 12 extending between collars 14, 16. Each arm 12 may be separated from one another by spacing or opening 20. Moreover, each arm 12 may be aligned parallel with one another although this is not necessary. Anchor 10 may define lumen 18 through the length of anchor 10 to allow for the passage of one or more sutures therethrough.

FIG. 1B shows a perspective view of anchor 10 of FIG. 1A in an anchoring or expanded configuration 10'. In such a configuration, proximal collar 14 and distal collar 16 are advanced towards one another such that the middle section 22 of arms 12 extend radially outwardly. Anchor 10' may be made from various materials, e.g., spring stainless steel, but is preferably made from a shape memory or superelastic alloy, e.g., nitinol. The anchor may thus be shaped and heat-set such that it self-forms or automatically configures itself from the delivery configuration 10 to the expanded configuration 10' upon release of a constraining force, e.g., when the anchor is ejected from its delivery needle or catheter, as described further below. Alternatively, the anchor may be configured to self-form into its expanded configuration 10' upon the application of some activation energy to the anchor, e.g., electrical energy, heat from the surrounding tissue, etc.

Upon expanding, the arms 12 of anchor 10' may extend radially outwardly such that spacing or opening 20' is defined between adjacent arms 12. The spacing 20' is preferably created to minimize the contact area between the anchor body and the underlying tissue surface to allow for greater blood flow in the tissue and to inhibit necrosis of the tissue.

When anchor 10' contacts the tissue surface, proximal collar 14 and proximal section 24 of arm 12 lay against the tissue while distal section 26 of arm 12 extends away from the tissue surface. Although seven arms 12 are shown in this example, the number of arms is not intended to be limiting and may be varied, as described in further detail below. Moreover, the configurations of proximal 24, distal 26, and middle section 22 of arms 12 may also be varied and is also described in further detail below.

Deploying the anchors against, into, or through the tissue may be accomplished in a number of ways. One example is shown in FIG. 2A, which shows a cross-section of an anchor delivery system 30 in proximity to tissue fold F. Tissue fold F may comprise a plication of tissue created using any number of tissue plication devices. Examples of such devices which may be utilized are described in further detail in U.S. patent application Ser. No. 10/735,030 filed Dec. 12, 2003. Tissue fold F may be disposed within a gastrointestinal lumen, such as the stomach, where tissue wall W may define the outer or serosal layer of the stomach. The anchor delivery assembly may generally comprise launch tube 32 and needle 40 slidingly disposed within the launch tube lumen. Needle 48 may generally be configured as a hollow needle having a tapered or sharpened distal end to facilitate its travel into and/or through the tissue.

Delivery push tube or catheter 34 may be disposed within launch tube 32 proximally of basket anchor 10, which is shown in a compressed delivery configuration with a relatively low profile when disposed within needle lumen 42 of needle 40. A single basket anchor 10 is shown disposed within needle 40 only for illustrative purposes and is not intended to be limited by the number of basket anchors; rather, any number of basket anchors may be disposed within needle lumen 42 as practicable depending upon the desired procedure and anchoring results.

Once launch tube 32 has been desirably positioned with respect to tissue fold F, needle 40 may be urged or pushed into or through tissue fold F via needle pushrod or member 44 from its proximal end. As shown in FIG. 28, basket anchor 56 has been urged or ejected from needle 40 and is shown in its radially expanded profile for placement against the tissue surface. In such a case, a terminal end of suture 66 may be anchored within the distal collar anchor 64 and routed through tissue fold F and through, or at least partially through, proximal anchor 56, where suture 38 may be cinched or locked proximally of, within, or at proximal anchor 56 via any number of cinching or locking mechanisms 68. Proximal anchor 56 is also shown in a radially expanded profile contacting tissue fold F along tissue contact region 54. Locking or cinching of suture 38 proximally of proximal anchor 56 enables the adequate securement of tissue fold F.

A single suture or flexible element 38 (or multiple suture elements) may connect proximal anchor 56 and distal anchor 64 to one another through tissue fold F in the case of a single tissue fold F. If additional tissue folds are plicated for securement, distal anchor 46 may be disposed distally of at least one additional tissue fold F' while proximal anchor 56 may be disposed proximally of tissue fold F. As above, suture 38 may be similarly affixed within distal anchor 46 and routed through proximal anchor 56, where suture 38 may be cinched or locked via cinching or locking mechanism 68, as necessary. Locking mechanism 68 may be further configured to apply a locking force upon the suture 38 such that the anchors located upon both sides of tissue fold F (or tissue folds F and F') may be advanced towards one another while cinching the tissue plication(s). Suture or flexible element 38 may comprise various materials such as monofilament, multifilament, or any other conventional suture material, elastic or elastomeric materials, e.g., rubber, etc.

If tissue folds F and F' are to be positioned into apposition with one another, distal anchor 46 and proximal anchor 56 may be approximated towards one another. Proximal anchor 56 is preferably configured to allow suture 38 to pass freely therethrough during the anchor approximation. However, proximal anchor 56 is also preferably configured to prevent or inhibit the reverse translation of suture 38 through proximal anchor 56 by enabling uni-directional travel of anchor 56 over suture 38. This cinching feature thereby allows for the automated locking of anchors 46, 56 relative to one another during anchor approximation. Aspects of anchor positioning relative to tissue and various examples of cinching or Socking mechanisms may be seen in further detail in U.S. patent application Ser. Nos. 10/840,950; 10/841,245; 10/840,951; and 10/841,411, each of which was filed May 7, 2004 and each being incorporated herein by reference in its entirety.

Figure 2B:
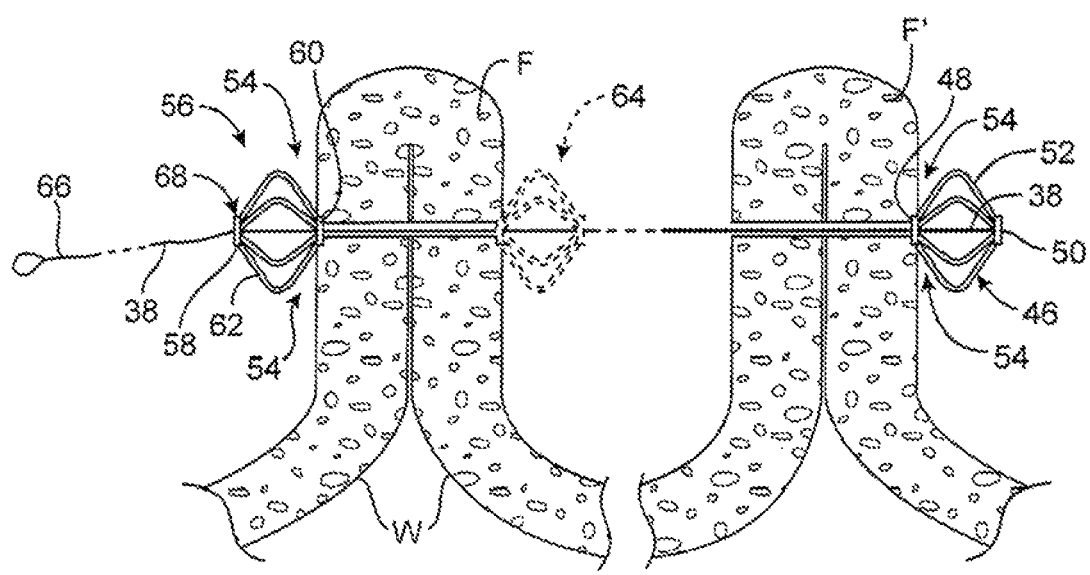
FIG. 2B shows a cross-sectional side view of examples of how basket anchors may be utilized in anchoring tissue plications.

The anchors, as described above, may be seen in FIG. 2B to each have proximal collars 48, 58 and respective distal collars 50, 60 with struts or arms 52, 62 extending therebetween. As described above, the basket anchors are preferably reconfigurable from a low profile delivery configuration to a radially expanded deployment configuration in which a number of struts, arms, or mesh elements may radially extend once released from launch tube 32 or needle 40. Materials having shape memory or superelastic characteristics or which are biased to reconfigure when unconstrained are preferably used, e.g., spring stainless steels, Ni—Ti alloys such as Nitinol, etc.

The basket anchors are illustrated as having a number of reconfigurable struts or arm members extending between a distal collar and proximal collar; however, this is intended only to be illustrative and suitable basket anchors are not intended to be limited to baskets only having struts or arms, as will be described in further detail below. Examples of suitable anchors are further described in detail in the references which have been incorporated by reference above as well as in U.S. patent application Ser. No. 10/612,170 filed Jul. 1, 2003, which is also incorporated herein by reference in its entirety.

As mentioned above, the anchor preferably exerts a force sufficient to maintain or secure a tissue plication yet still allows for adequate blood flow to occur within the tissue underlying the anchor. When the anchor has been configured into its expanded configuration, a load or force may be applied to the anchor until the anchor has been optimally configured to accommodate a range of deflections while the anchor itself maintains or exerts a substantially constant force against the tissue. Anchor deflection may occur, e.g., when the proximal and distal collars of an anchor have been advanced or urged towards one another such that the arms or struts extending therebetween are at least partially deflected. Moreover, anchor deflection may be due to various movements of the tissue attributable to, e.g., peristalsis, patient movement, weight of the gastrointestinal organ itself, etc.

Figure 3A:
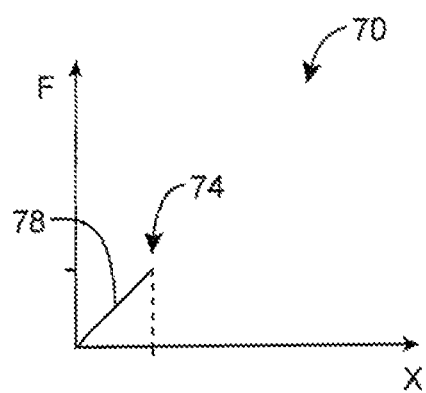
FIGS. 3A and 3B show a graph of initial displacement or deflection versus exerted force and an example of a tissue anchor correspondingly displaced, respectively.
Figure 3B:
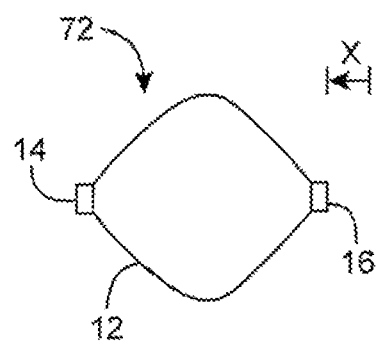
Figure 4A:
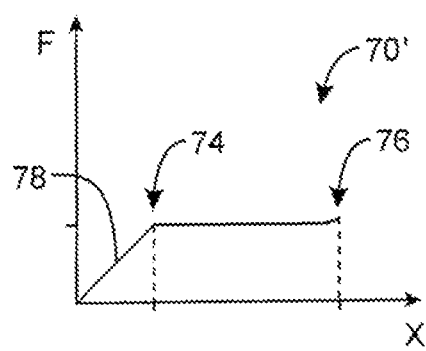
FIGS. 4A and 4B show the graph illustrating an optimal range of anchor deflection where the exerted force by the anchor remains substantially constant and the correspondingly compressed anchor, respectively.
Figure 5A:
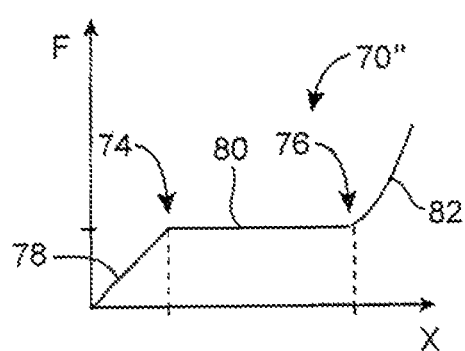
FIGS. 5A and 5B show the graph illustrating the rising force for an over compressed anchor and the correspondingly compressed anchor, respectively.

FIGS. 3A, 4A, and 5A illustrate an example of how the progressive deflection of an anchor may result in a substantially constant force exerted by the anchor itself. As shown in the graph 70 of FIG. 3A, an amount of anchor deflection, x, is plotted against the resulting force, F, exerted by the anchor. FIG. 3B shows an illustrative profile of an exemplary anchor; proximal collar 14, distal collar 16, and struts 12 are shown for reference. With proximal collar 14 stationary relative to the anchor, distal collar 16 may be urged initially at some distance, x. The anchor may thus be configured into an initial deflected configuration 72, as shown in FIG. 3B. The deflection may be induced via a suture or flexible member urging the collars towards one another, e.g., during tissue plication formation or securement.

Figure 4B:
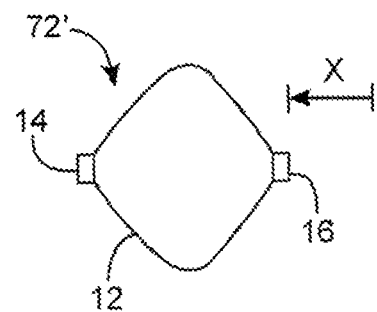

FIG. 3A shows the corresponding increase in force 78 over the initial loading of the anchor through deflection, x. As the deflection of the anchor is increased, the anchor may be configured into a configuration 72', as shown in FIG. 4B, where the increasing force exerted by the anchor passes an inflection point 74 and enters an "optimal" window or range 80 in which the exerted force remains relatively constant over a range of deflections, as shown by the loading graph 70' in FIG. 4A. Within this range 80 of deflections, the amount of force exerted by the anchor may be substantially constant, i.e., relatively constant or increasing at a rate lower than the rate of initial loading 78 or rate of "over" loading 82 the anchor, as shown below.

Figure 5B:
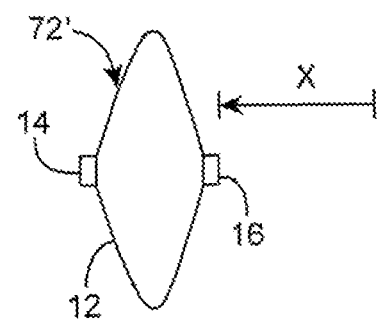

At the upper portion of range 80, the force exerted by the anchor may begin to increase relative to the deflection, as indicated by loading curve 82 beyond inflection point 76 shown in the loading graph 70" of FIG. 5A. FIG. 5B shows the corresponding over-loaded anchor configuration 72" where the anchor may be seen as having been deflected beyond the configuration shown in FIG. 4B. The force representing the over loading of the anchor may increase steadily until the anchor is forced into a configuration where proximal 14 and distal 16 collars have been urged towards one another to the point where they contact one another.

Knowing the anchor deflection-to-exerted force characteristics for a given anchor, one may load an anchor with a tension or compression force such that subsequent deflections of the underlying tissue being anchored occur within specified ranges, such as the optimal range. For instance, an anchor may be pre-loaded such that tissue fluctuations or movements occur within the optimal window or range where the force exerted by the anchor remains relatively constant over a range of deflections. This in turn may ensure that the underlying tissue is not subject to over-compression by the anchors.

One method for limiting the loading or pre-load force upon an anchor may involve including a post or stop 98 in the anchor body, as shown in the anchor variation 90 of FIG. 6A, which shows a partial cross-sectional view of the anchor. Post or stop 98 may be integrally formed with proximal collar 94 and extend distally between struts 92. Alternatively, post 98 may also be fabricated separately and attached through one of a number of mechanical methods to proximal collar 94, e.g., adhesives, threading, interference fitted, etc. Post 98 may define a lumen to allow suture 38 to pass through the anchor 90. The anchor 90 may be loaded via suture 38 until the anchor 90 is configured to fall within the optimal window or range. As the underlying tissue moves, the anchor may be deflected accordingly; however, if the anchor is subjected to large deflections by the tissue, post 98 may prevent distal collar 96 of the anchor from over-compressing the anchor, as shown in the compressed configuration 90' of FIG. 6B.

Another variation which may be utilized to limit the loading of the anchor during anchor placement and tensioning against the tissue is shown in the partial cross-sectional views of FIGS. 7A and 7B. Tensioning assembly 100 may be seen proximally of anchor proximal collar 14 contained within the delivery push tube or catheter 102. An elongate member 104, e.g., a tubular member, may extend through catheter 102 and define a specified region 108 having a known coefficient of friction near or at the distal end of elongate member 104. Frictional region 108 may be an area of the elongate member 104 having a separate material of known frictional coefficient coated or adhered thereon. Alternatively, the frictional region 108 may be integral with elongate member 104 and may simply be abraded or roughened to alter the frictional coefficient of region 108.

Suture 38 may be attached at attachment point 106 to the distal end of elongate member 104 and may further extend into the anchor. As elongate member 104 is slid proximally through catheter 102 to impart a tension or load upon the anchor via suture 38, member 104 may pass through at least one or more regions which are in intimate contact around member 104. The regions in contact with member 104 may comprise at least a first frictional area 110 having a known first frictional coefficient. As elongate member 104 is withdrawn proximally in the direction of travel 118, frictional region 108 may slide against first frictional area 110 and generate a first frictional force 1, as indicated by plot 120 on the graph of FIG. 8A. The generated first frictional force 1 may be detected through any number of various devices and may be used to indicate to the operator that anchor is being loaded.

As elongate member 104 is withdrawn further proximally, frictional region 108 may be withdrawn proximally of first frictional area 110 and against second frictional area 112, which may also have a known second frictional coefficient different from the first frictional coefficient of the first frictional area 110, as shown in FIG. 7B. A length of first frictional area 110 may accordingly be configured to correspond to the length of suture needed to load the anchor info its optimal configuration. As elongate member 104 slides against second frictional area 112, a second frictional force II may be generated which may be less than the first frictional force FIG. 8B shows the drop in the generated frictional force as indicated by plot 122. This change in the detected force may thus be utilized to indicate to the Operator that anchor has been configured within an optimal range of deflections. Once the anchor has been optimally configured, the suture may be secured relative to the anchor using any number of the cinching and/or locking methods as described in U.S. patent application Ser. Nos. 10/840,950; 10/841,245; 10/840,951; and 10/841,411, each being incorporated by reference above.

To prevent elongate member 104 from being over-withdrawn proximally and from over-compressing the anchor, protrusions 114 may project from elongate member 104 and corresponding stops 116 may project from within catheter 102. Protrusions 114 and the corresponding stops 116 may accordingly be configured to prevent the further withdrawal of elongate member 104 from catheter 102. Moreover, although first 110 and second 112 frictional areas are shown in this example, a single frictional area or additional areas may be utilized, each having a different coefficient of friction.

Furthermore, first 110 and second 112 frictional areas may be fabricated from different materials or they may be made from the same or similar material as catheter 102 and simply coated or covered with the various materials. For instance, first frictional area 110 may be fabricated from a material such as PEBAX®, while second frictional area 112 may be fabricated from a material such as HDPE. Alternatively, rather than utilizing a coating or covering, first 110 and second 112 frictional areas may be textured or abraded to create surfaces having differing frictional coefficients. The types of materials utilized or the types of surface textures created or even the number of different frictional areas are not intended to be limiting but are merely presented as possible variations. So long as a detectable change in the generated frictional force between elongate member 104 and the surrounding frictional region is created, any number of materials or regions may be utilized.

Figure 9:
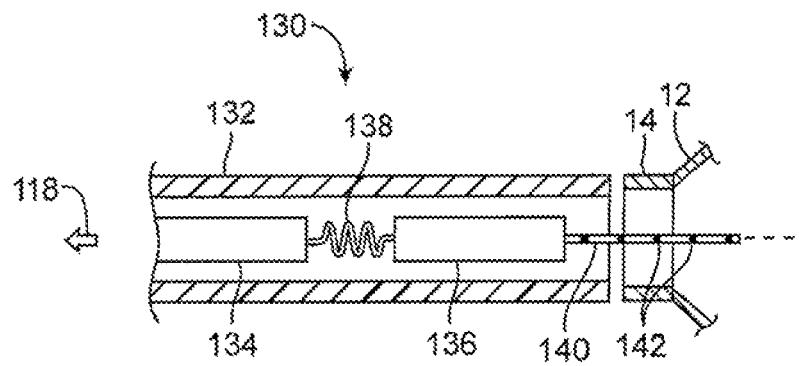
FIG. 9 shows a partial cross-sectional view of another variation of an anchor loading mechanism which utilizes a spring member having a known spring constant.

FIG. 9 shows another anchor tensioning variation in assembly 130. As shown, the tensioning assembly may be contained within delivery push tube or catheter 132. An elongate pull member 134, which may be manipulated via its proximal end by the user, may be connected to a tensioning block or member 136 via spring member 138. Pull member 134 and tensioning block or member 138 may generally be formed from a variety of biocompatible metals, e.g., stainless steel, Nitinol, etc., or plastics provided that the material is rigid relative to spring member 138 and suture 140 and will not affect the measurement of the linear deformation of spring member 138. Spring member 138 may generally comprise a linear spring element having a known spring constant. Suture 140 may be attached to a distal end of block 136 and further routed into or through distally located the tissue anchor.

During use in loading the tissue anchor, pull member 134 may be withdrawn proximally by its proximal end. As it is withdrawn, the force required to withdraw member 134 may be measured. With the spring constant and the measured force, the amount of linear deflection may be calculated to determine the amount of deflection the anchor has undergone. Alternatively, suture 140 may be marked uniformly at known distances with markings or gradations 142. As the pull member 134 is withdrawn, the length of suture 140 withdrawn into catheter 132 may be measured visually using, e.g., a video endoscope, by counting the number of gradations 142 passing into catheter 132. Knowing the linear distance and the spring constant, the anchor deflection may be calculated. Thus, measurement of either the force required to withdraw member 134 or the linear distance traveled by suture 140 may be utilized to determine the anchor deflection. With the known deflection, the assembly may be configured to indicate when the anchor has been deflected to a predetermined level, e.g., when the anchor has been deflected within the optimal range.

Figure 10:
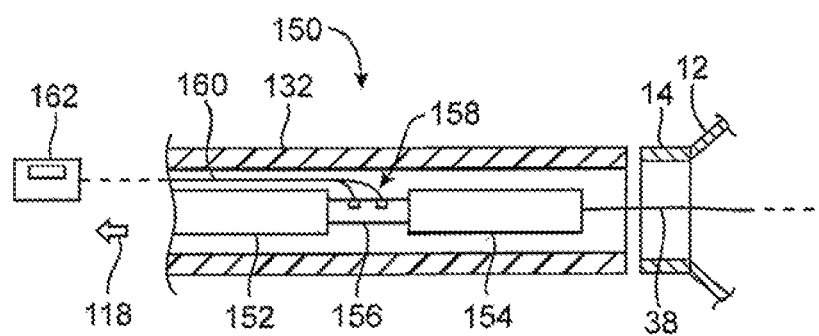
FIG. 10 shows a partial cross-sectional view of another variation of an anchor loading mechanism utilizing a strain gauge for measuring the strain, and the resultant load, exerted upon the anchor.

Another alternative of an anchor tensioning assembly is shown in the partial cross sectional view of FIG. 10. Assembly 150 may generally comprise an elongate pull member 152 connected to tensioning block or member 154. Pull member 152 and tensioning block 154 may be fabricated from the same or similar materials as described above. A third element 156 having a known length which is less rigid than pull member 152 or tensioning block 154 may connect the two. This element 156 may have strain gauge 158 attached thereto for measuring the strain of the element 156 as pull member 152 is withdrawn proximally. The signals detected from the strain gauge 158 may be transmitted via wires 160 to a processor and/or display 182 located externally of the patient to record and process the strain information. With the known original length of element 156 and the measured strain, the length of linear deflection of the attached anchor may be calculated. With this information, the anchor deflection may be determined and the assembly 150 may be configured to indicate when the anchor has been deflected to a predetermined level to ensure optimal loading of the anchor.

Figure 11:
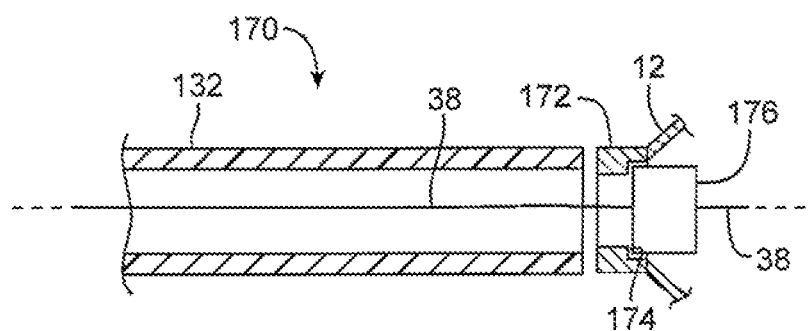
FIG. 11 shows a cross-sectional view of another variation of an anchor loading mechanism which utilizes a stop for limiting the anchor compression to a predetermined limit.

Yet another alternative is shown in the partial cross-sectional view of FIG. 11. In this variation, assembly 170 may simply comprise an anchor having a stepped proximal collar 172 to define a step or detent 174 which prevents the passage of stop member 176 contained within the anchor. The length of suture 38 extending from stop member 176 to the attachment point within the anchor may be of a predetermined length such that when stop member 176 is seated against proximal collar 172, the suture length may compress the anchor into a predetermined deflection level. This deflection level may be preset to configure the anchor to any desired configuration, as described above.

Figure 12A:
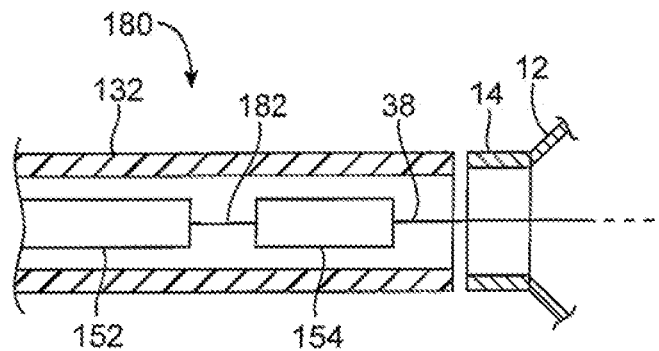
FIGS. 12A and 12B show partial cross-sectional views of another variation of an anchor loading mechanism utilizing a fuse-like device set to break or release upon reaching a predetermined toad.
Figure 12B:
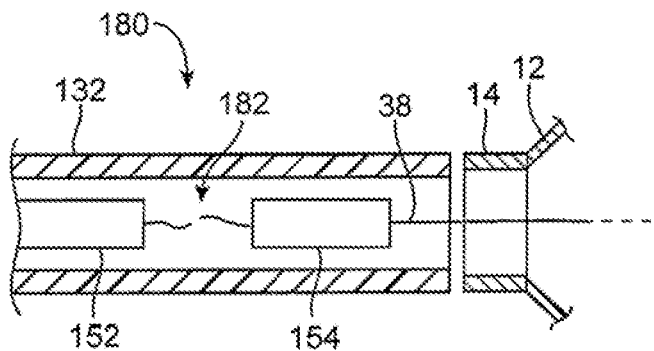

Yet another variation is shown in the partial cross-sectional views of FIGS. 12A and 12B. Assembly 180 may generally comprise elongate pull member 152 and tensioning block or member 154, as above. However, a fuse material 182, i.e., a length of material having a preset or known failure or break strength, may be used to join pull member 152 and tensioning block 154. This fuse 182 may generally comprise a variety of materials, e.g., silk, stainless steel, etc., provided that the failure strength of fuse 182 is less than the force necessary for causing necrosis of the tissue to be anchored. For instance, a fuse 182 may be configured to break at a pressure of e.g., 2 psi.

In operation, as elongate pull member 152 is withdrawn proximally, tensioning block 154 may be withdrawn as it is pulled by fuse 182. As the anchor becomes compressed and the force on fuse 182 increases, once the force reaches the pre-set limit, the fuse 182 may break, as shown in FIG. 12B, thereby preventing further compression of the anchor and limiting the force applied onto the tissue.

Figure 13A:
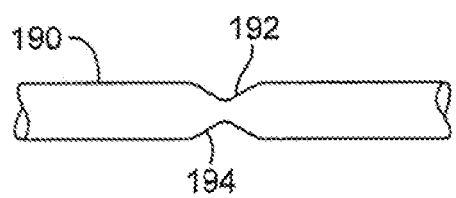
FIGS. 13A and 13B show side views of various notched fuse-members which may be utilized with the variation of FIGS. 12A and 12B.
Figure 13B:

Fuse 182 may be comprised from various materials. Optionally, the fuse may be altered to modify its break strength, e.g., by including multiple notches 192, 194, as seen in fuse variation 190 of FIG. 13A to create a necked-down region. Alternatively, a single notch 198 may be utilized, as seen in fuse variation 198. The notches may be defined on the fuse to alter the break strength or to ensure the breakage or failure of the fuse.

Figure 14A:
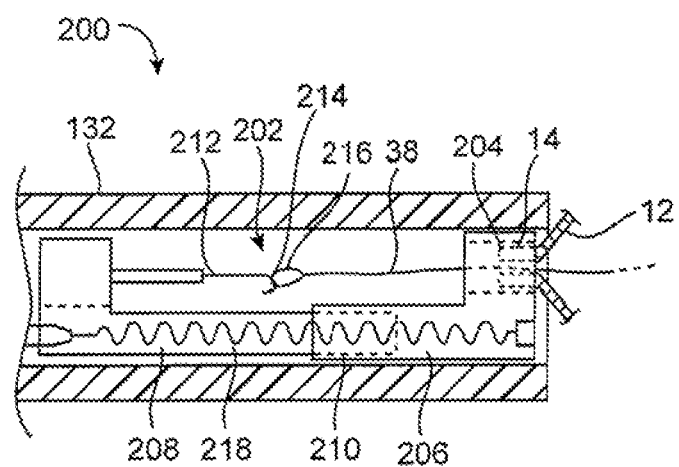
FIG. 14A shows a partial cross-sectional side view of a device which may be used to apply the load upon the loading mechanism.

When tensioning the anchors using any of the devices or methods described herein, various mechanisms may be used to apply the tensioning force on the suture. One mechanism is shown in the partial cross-sectional view of FIG. 14A, which shows a tensioning assembly 200 positioned within catheter 132. The assembly may generally comprise tensioning mechanism 202, which may have an anchor interlace member 208 and a tensioning interface member 208 configured to slide relative to one another within catheter 132. Anchor interface member 206 may define anchor collar channel 204 configured to receive and temporarily hold the proximal collar 14 of an anchor to be loaded.

Tensioning interface member 208 may be configured to slide relative to anchor interface member 206 via a slidable connection 210. Tensioning member 208 may also comprise suture coupler 212 and hook 214 for holding terminal end 216 of suture 38 during a tensioning procedure. Tensioning member 208 and anchor member 206 may be urged towards one another via some biased member, e.g., spring member 218, having a known spring constant, in use, when a tissue anchor is ready to be loaded, the proximal collar 14 may be held within anchor collar channel 204 and with terminal end 216 of suture 38 retained by hook 214, tensioning member 208 may be withdrawn proximally relative to anchor member 206 until the desired tensioning level is reached. Other variations utilizing, e.g., a strain gauge, for measuring the tension applied or utilizing, e.g., graspers, rather than a hook may be utilized to desirably tension the tissue anchors.

Figure 14B:
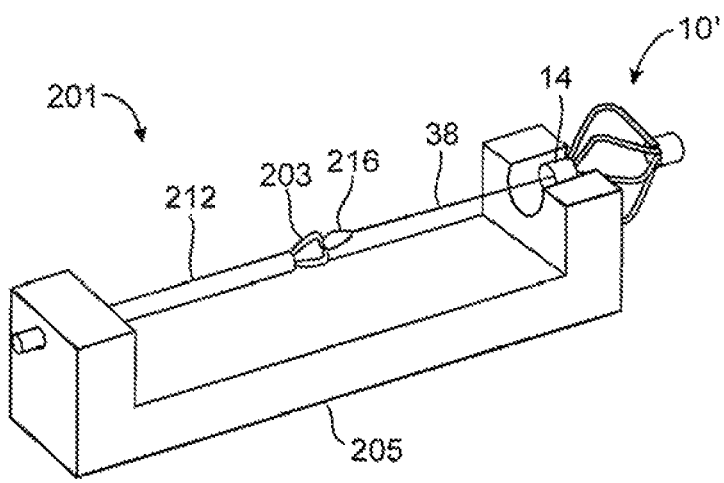
FIG. 14B shows a perspective view of an alternative loading mechanism.

FIG. 14B shows a perspective view of an alternative tensioning assembly 201 which may be used to apply the load upon the anchor. This assembly 201 may be utilized in conjunction with any of the tension measuring apparatus described herein. As shown, anchor 10' may be positioned at the distal end of base 205 with suture 38 extending proximally while being tensioned via suture coupler 212, as in assembly 200 described above. Graspers 203, which may be articulated to open or close, may be used to hold suture terminal end 216 while tensioning anchor 10'. Base 205 may be configured to extend longitudinally, as above, or suture coupler 212 may be configured to slide proximally to tension the anchor 10'.

Figure 14C:
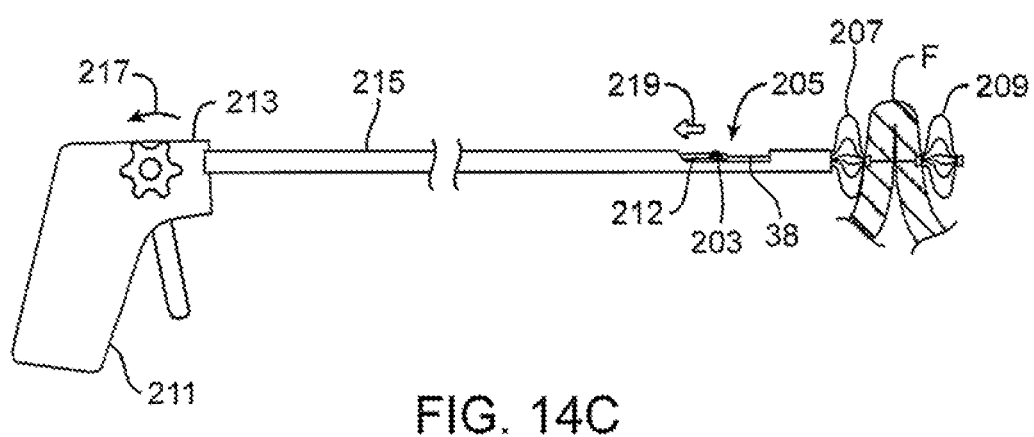
FIG. 14C shows a side view of an assembly in which the loading mechanism may be placed for applying the load upon the anchors.

FIG. 14C shows a device which may be used by the surgeon or operator outside a patient body to tension the anchors positioned within the body. Generally, the handle assembly may comprise handle 211 and a hollow elongate shaft 215 extending from the handle 211. Shaft 215 may function much like a laparoscopic shaft if shaft 215 is rigid; alternatively, shaft 215 may be configured to be flexible for advancement within or through an endoscope or other working lumen, if so desired. A tensioning assembly, as described above, may be positioned within the lumen of shaft 215 near or at the distal end of shaft 215 and the control mechanisms, e.g., suture coupler 212, may be actuatable from handle 211. In one variation, control wheel or ratchet control 213, which may be located on handle 211, may be rotated in the direction of arrow 217 to actuate base 205 or suture coupler 212 in a proximal direction, as indicated by arrow 219. Tensioning suture 33 with ratchet control 217 may draw anchors 207, 209 towards one another to secure tissue fold F while also applying an appropriate load upon anchors 207, 209.

Various other factors of the tissue anchors may be modified to affect the tensioning and loading characteristics when deflecting the anchors. Moreover, some of the factors may also affect the interaction of the anchor with respect to the tissue in ensuring that the tissue is not over-compressed and that adequate blood flow may occur within the tissue directly beneath the anchor.

One factor may include varying the number of arms or struts of the anchor. For instance, the anchor may be configured to have, e.g., seven struts or arms 12 which deflect about the proximal 14 and distal 16 collars, as shown in the flattened view of one anchor variation 220 in FIG. 15A. FIG. 15B shows a side view of the flattened anchor 220 while FIG. 15C shows a perspective view of the anchor 220 in an unexpanded delivery configuration.

FIG. 16A shows another variation of anchor 230 in a flattened view with struts or arms 232 extending between proximal collar 238 and distal collar 238. In this variation, five arms 232 may be utilized to increase the spacing 234 defined between adjacent arms 232. The increased spacing 234 may be utilized to ensure the blood flow in the tissue beneath the tissue. FIG. 16B shows a side view of the flattened anchor 230 and FIG. 16C shows a perspective view of anchor 230 in its unexpanded delivery configuration. Other variations are discussed below.

Aside from varying the number of struts or arms, the configuration of the arms themselves may be varied. As seen in FIG. 16A, cross-sections of an individual arm 232 may be viewed for discussion purposes at three sections, proximal I, middle II, and distal III portions of the arm 232, FIGS. 17A to 17J show examples of possible variations for cross-sectional areas of an arm at each section, proximal I, middle II, and distal III. These figures are not intended to be limiting but are merely intended as examples of possible arm configurations.

Figure 17A:
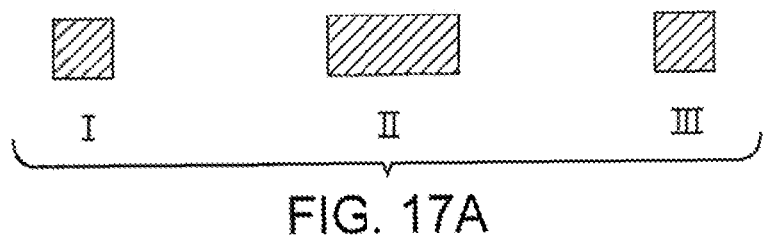
FIGS. 17A to 17J show cross-sectional end views of the proximal (I), middle (II), and distal (III) portions of a single anchor strut or arm showing some of the various shapes that the anchor strut or arm may be configured.

FIG. 17A shows an arm configuration where sections I and III may be square in shape with the middle section II rectangular.

Figure 17B:
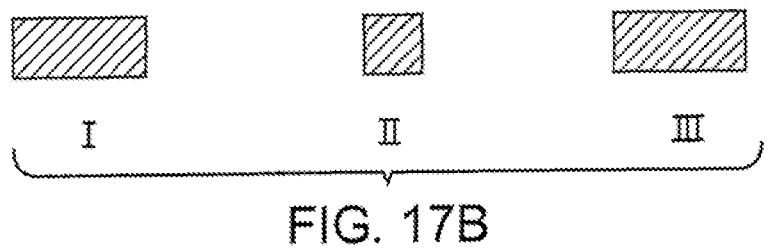

FIG. 17B shows an arm configuration where sections and III may be rectangular in shape with the middle section II square.

Figure 17C:
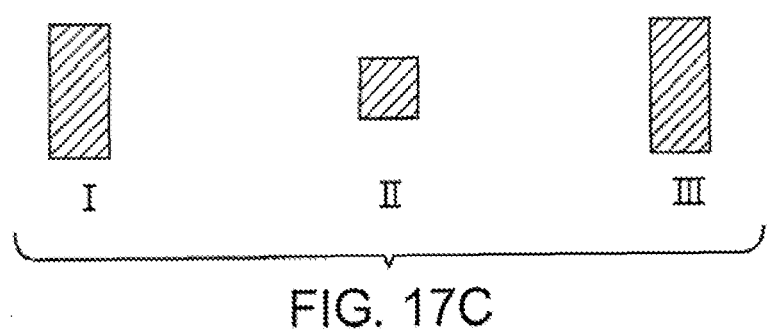

FIG. 17C shows an arm configuration where sections I and III may be rectangular in shape in a transverse direction with the middle section II square.

Figure 17D:
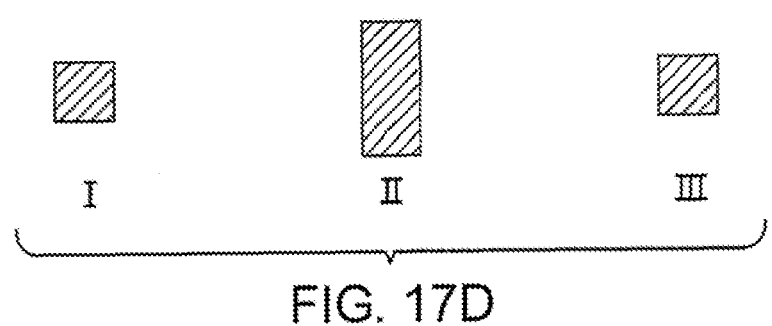

FIG. 17D shows an arm configuration where sections I and III may be square in shape with the middle section II rectangular in a traverse direction.

Figure 17E:
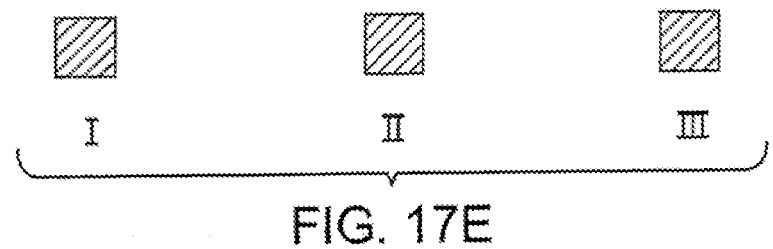

FIG. 17E shows an arm configuration where all sections I, II, and III may be square in shape.

Figure 17F:
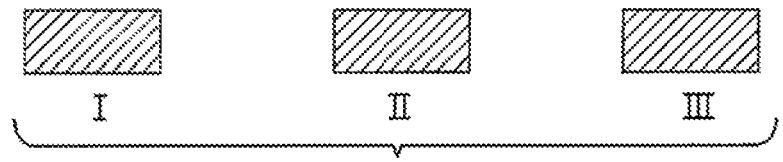

FIG. 17F shows an arm configuration where all sections I, II, and III may be rectangular in shape.

Figure 17G:
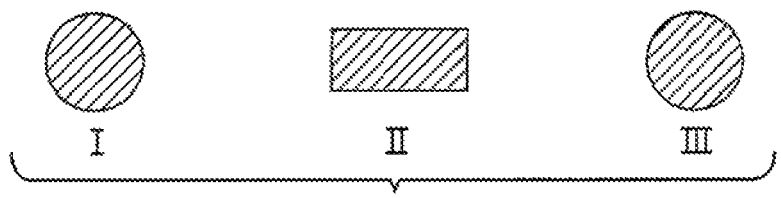

FIG. 17G shows an arm configuration where sections I and III may be circular in shape with the middle section II rectangular.

Figure 17H:
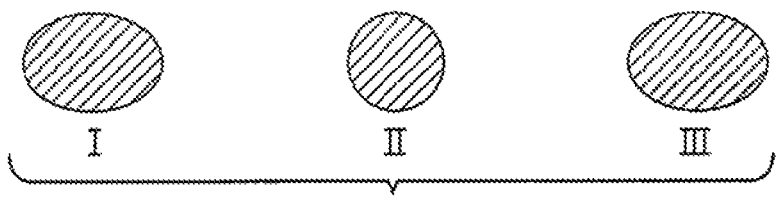

FIG. 17H shows an arm configuration where sections I and III may be elliptical in shape with the middle section II circular.

Figure 17I:
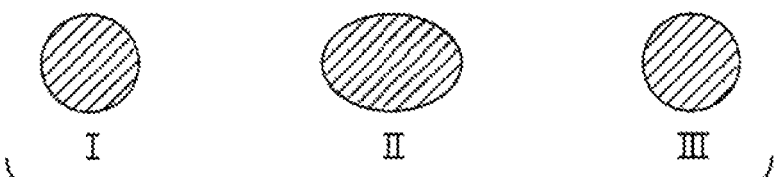

FIG. 17I shows an arm configuration where sections I and III may be circular in shape with the middle section II elliptical.

Figure 17J:
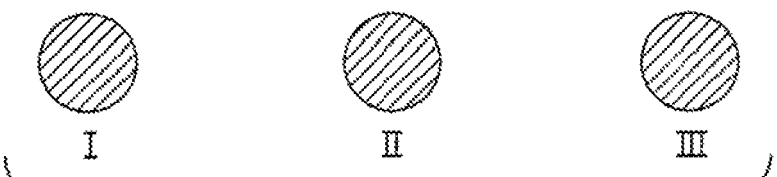

FIG. 17J shows an arm configuration where all sections I, II, and III may be circular in shape.

As mentioned above, varying the number of struts or arms may be utilized to vary not only the contact area with respect to the underlying tissue, but to also affect the optimal loading characteristics of the anchor. Aside from the number of arms, the positioning of the arms may also be utilized. For example, FIGS. 18A to 18F show end views of anchor variations having a number of varying arms and arm positions. Again, these figures are not intended to be limiting but are merely intended as examples.

Figure 18A:
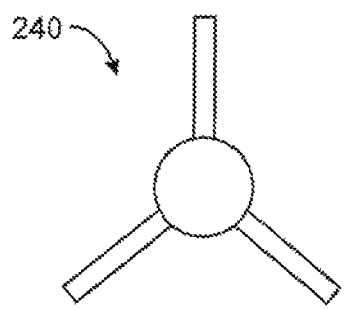
FIGS. 18A to 18F show examples of end views of anchors having an increasing number of struts or arms.

FIG. 18A shows the end view of an anchor 240 having 3 arms uniformly spaced apart.

Figure 18B:
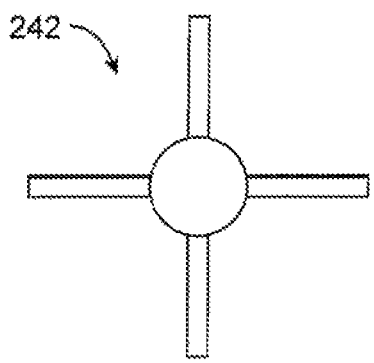

FIG. 18B shows the end view of an anchor 242 having 4 arms uniformly spaced apart.

Figure 18C:
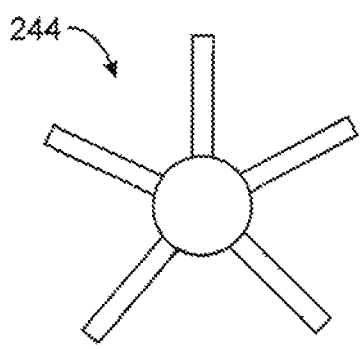

FIG. 18C shows the end view of an anchor 244 having 5 arms uniformly spaced apart.

Figure 18D:
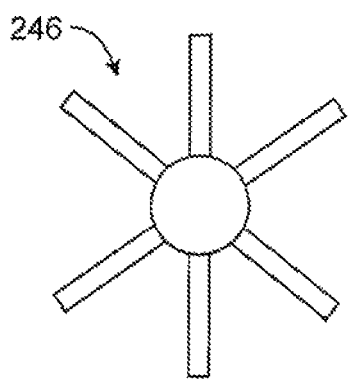

FIG. 18D shows the end view of an anchor 248 having 6 arms uniformly spaced apart.

Figure 18E:
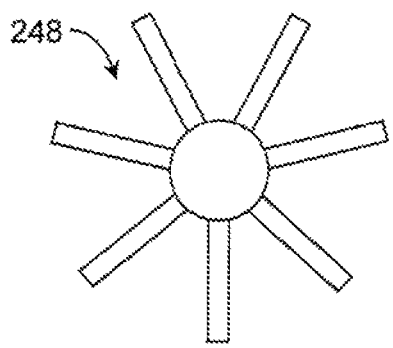

FIG. 18E shows the end view of an anchor 248 having 7 arms uniformly spaced apart.

Figure 18F:
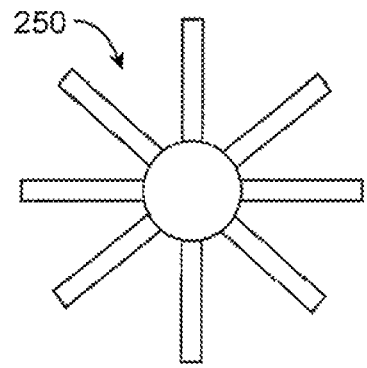

FIG. 18F shows the end view of an anchor 250 having 9 arms uniformly spaced apart.

Any number of arms may be utilized as practicable and although the arms in the above examples are uniformly spaced apart from one another, the spacing between the arms may be varied irregularly or arbitrarily provided that the spacing between the arms enable adequate blood flow in the underlying tissue.

Not only can the number of arms and spacing between the arms be varied, but also the arm configurations themselves. For instance, the arms may be preformed into various shapes depending upon the desired effects on the anchor loading characteristics. As above, these figures are not intended to be limiting but are merely intended as examples.

Figure 19A:
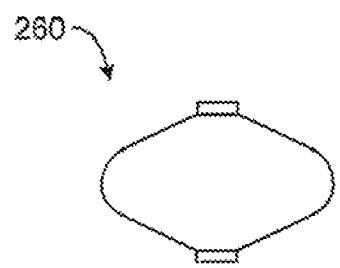
FIGS. 19A to 19F show examples of side views of anchors having various strut or arm configurations.

FIG. 19A shows an illustrative side view of anchor 260 having curved arms.

Figure 19B:
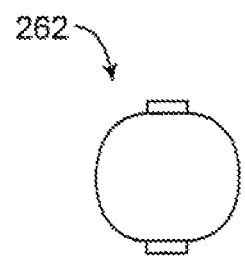

FIG. 19B shows an illustrative side view of anchor 282 having circularly-shaped arms.

Figure 19C:
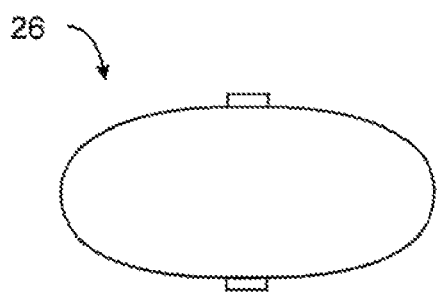

FIG. 19C shows an illustrative side view of anchor 264 having elliptically-shaped arms.

Figure 19D:
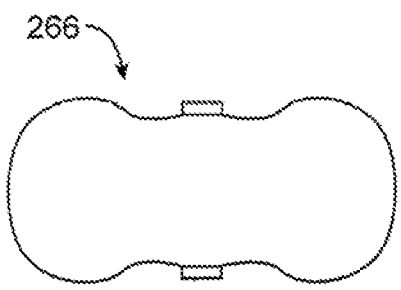

FIG. 19D shows an illustrative side view of anchor 266 having bow-shaped arms.

Figure 19E:
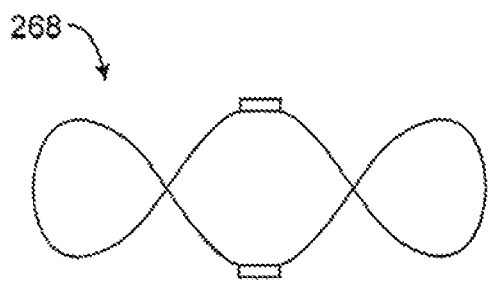

FIG. 19E shows an illustrative side view of anchor 268 having arms shaped into a figure-eight manner.

Figure 19F:
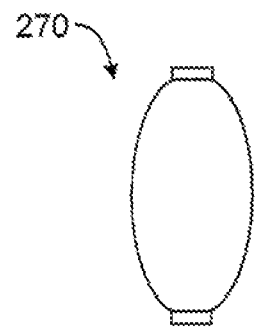

FIG. 19F shows an illustrative side view of anchor 270 having minimally-radiused arms.

Figure 20A:
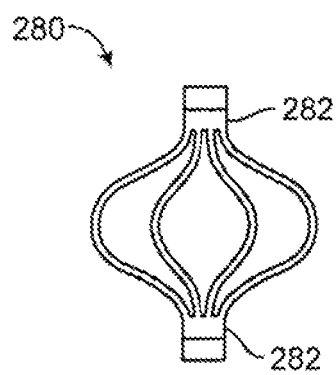
FIGS. 20A and 20B show side views of anchors having various configurations affected by the heights of the anchor collars.
Figure 20B:
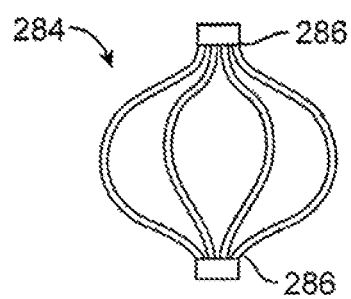

Aside from the arm shapes, the length of the collars may be varied as well. FIG. 20A shows anchor variation 280 having extended anchor collars 282, which may act to reduce the radius of the arms. FIG. 20B shows anchor variation 284 having reduced collars 288, which may act to increase the radius of the arms. As above, these figures are not intended to be limiting but are merely intended as examples.

Figure 21A:
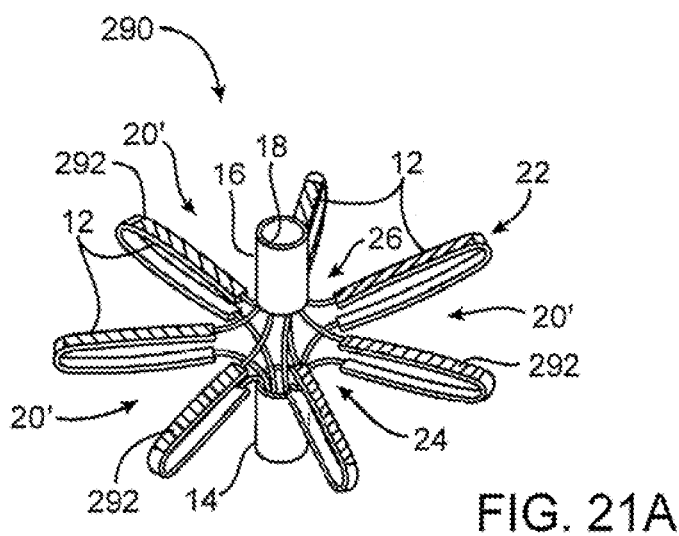
FIG. 21A shows a perspective view of an anchor in an expanded configuration having a protective coating or covering over at least a portion of the struts or arms.

When the anchors are deployed into or against the tissue, at least one portion of the anchor arms are generally against the tissue surface while another portion of the arms are exposed within the lumen. The exposed portions of the anchor may be optionally coated or covered with a material to protect against exposure to foreign materials, e.g., food or other object which may be ingested by the patient, other surgical tools, etc. Accordingly, as shown in the perspective view of anchor variation 290 in FIG. 21A, a biocompatible coating or covering 292 may be placed over the entire length of the anchor arms 12 or only along the portions of the arms 12 not against the tissue. The coating or covering 292 may be comprised from various materials, e.g., elastomers, plastics, etc.

Figure 21B:
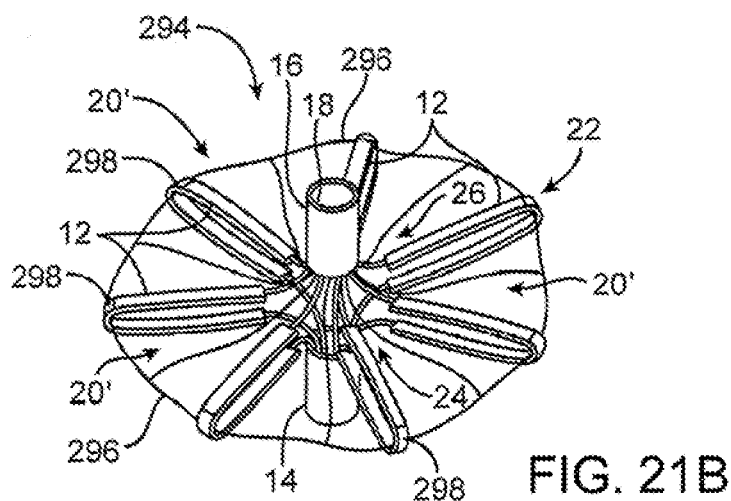
FIG. 21B shows a perspective view of another anchor having a protective covering or mesh over at least a portion of the anchor facing away from the tissue surface.
Figure 21C:
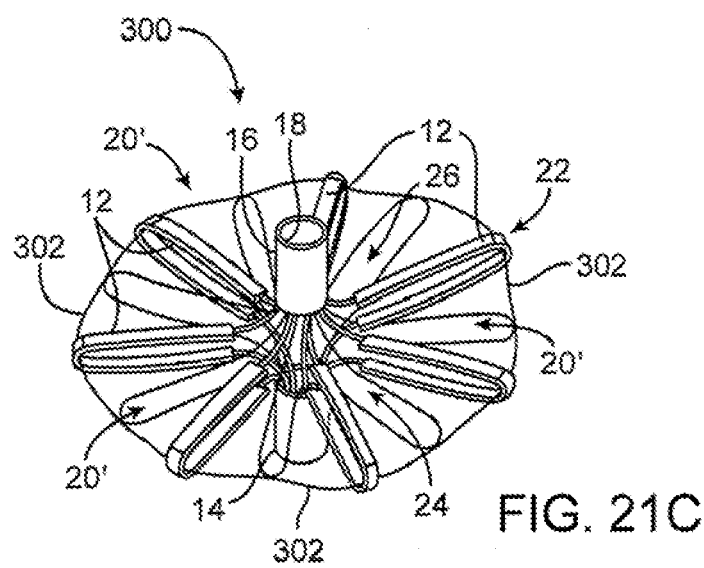
FIG. 21C shows a perspective view of another anchor having a protective covering or mesh over the entire anchor body.

Alternatively, a mesh or skirt-like covering 298 may be placed over the exposed portion of the anchor 294, as shown in FIG. 21B, which is attached to the anchor via attachment points 298 along each of some of the arms 12. Yet another alternative may be seen in anchor variation 300 in FIG. 21C in which the entire anchor itself may be covered with a distensible or expandable covering or mesh.

Figure 22A:
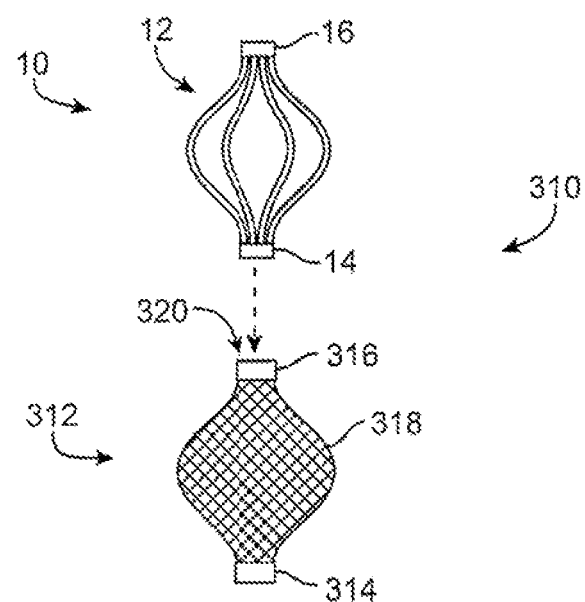
FIG. 22A shows an example of a combination hybrid basket assembly.

In yet another variation shown in FIG. 22A, a combination hybrid basket assembly 310 may generally comprise basket anchor 10, as previously described, which may be placed entirely within a basket anchor 312 comprised primarily of a mesh or distensible material, e.g., PTFE, PET, etc. Each anchor, i.e., basket anchor 10 and mesh anchor 312, may each be formed individually and basket anchor 10 may be positioned through mesh basket opening 320 such that basket anchor 10 is entirely enveloped by mesh 318 within mesh basket 312. Mesh basket 312 may be comprised generally of a mesh 318 having proximal 314 and distal 316 collars, as shown. Moreover, mesh 318 may be pre-formed to expand from a low profile configuration for delivery into an expanded configuration for deployment.

Figure 22B:
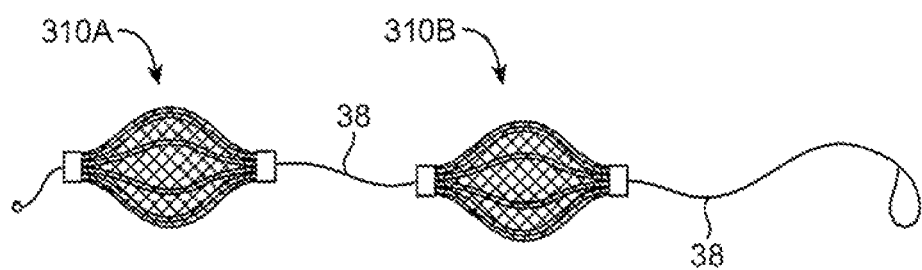
FIG. 22B shows the basket assembly of FIG. 22A formed with a second basket assembly with a length of suture routed therebetween for tissue securement.

When deployed for tissue securement, one or more hybrid basket assemblies, e.g., first basket assembly 310A and second basket assembly 310B as shown in FIG. 22B, may be interconnected via suture 38 such that suture 38 passes freely through one or both basket assemblies 310A, 310B.

Figure 23A:
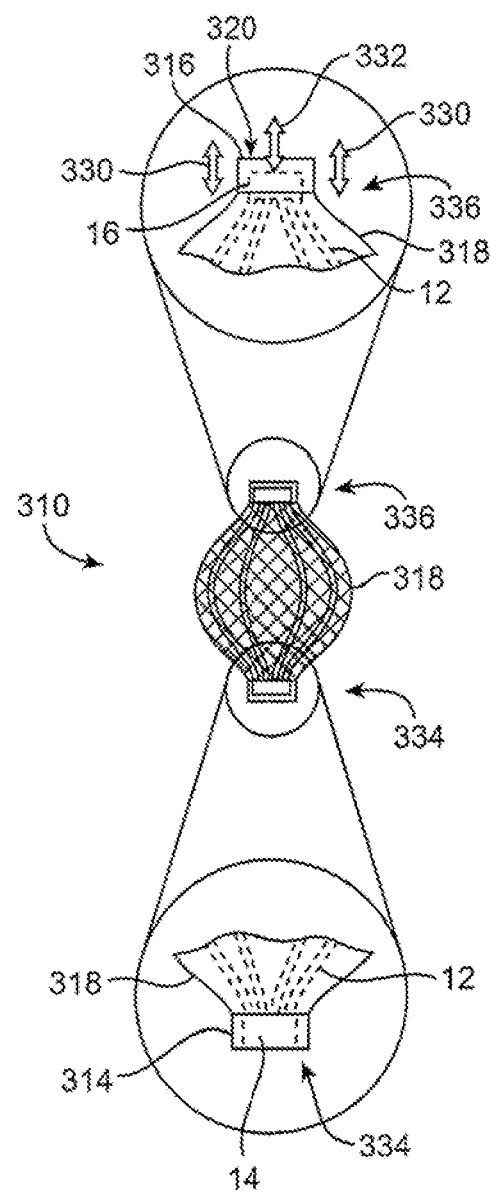
FIG. 23A shows the basket assembly of FIG. 22A with detail views of either collar ends.

Generally, basket anchor 10 may freely float within mesh basket 312 such that the proximal 14 and distal 16 collars of basket anchor 10 are freely moveable with respect to proximal 314 and distal 316 collars of mesh basket 312, as shown and described above. Alternatively, one or both ends of the anchor collars may be fused or formed to one another. For example, as shown in FIG. 23A, basket assembly 310 may be seen with detail views of either collar ends. In this example, distal collar 16 of basket anchor 10 may freely move, us shown by arrow 332, with respect to distal collar 316 of mesh basket 312 through mesh basket opening 320 at free-anchor end 336. Distal collar 318 may also freely move, as shown by arrows 330. The proximal collar 14 of basket anchor 10, on the other hand, may be fused, formed, welded, adhered, or otherwise attached to proximal collar 314 of mesh basket 312 at fused-anchor end 334 such that relative movement between the collars 14, 314 is prohibited or restrained.

Thus, when proximal collars 14, 314 at fused-anchor end 334 are placed against a tissue surface to be secured, distal collars 16, 316 at free-anchor end 336 may freely translate with respect to one another such that anchor assembly 310 may be fully cinched or compressed freely without any mismatched compression occurring between basket anchor 10 and mesh anchor 312. Alternatively, distal collars 16, 316 may also be fused or attached to one another such that movement of either collar ends ate fully constrained with respect to each anchor. In such an alternative, the compression rate of basket anchor 10 is preferably matched with that of mesh anchor 312.

Figure 23B:
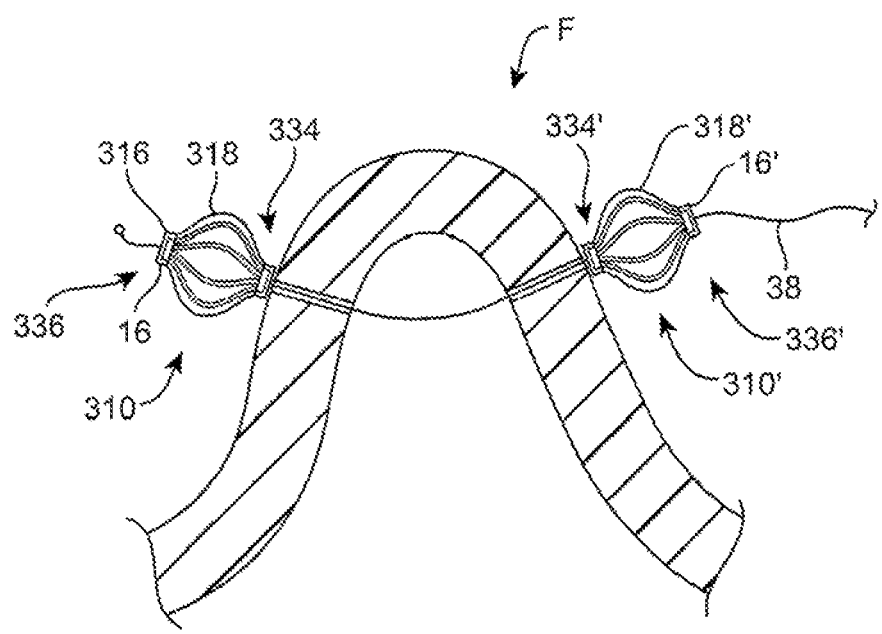
FIGS. 23B and 23C show the basket assembly of FIG. 23A in use with another similar anchor in an apposed configuration in approximating a portion of tissue info a serosa-to-serosa tissue fold.

An example of use for the fused hybrid anchors is shown in FIG. 23B. A distal hybrid anchor 310 having a basket anchor enclosed within mesh 318 may be deployed on a first side of a tissue region to be plicated, e.g., into a tissue fold F, as described above. The proximal collars 14, 314 of the hybrid anchor assembly 310 may be deployed such that fused-anchor end 334 rests against or abuts the surface of the tissue. With suture 38 passing through distal hybrid anchor 310 and through the dual-layers of tissue fold F, a proximal hybrid anchor 310', likewise having a basket anchor enclosed within mesh 318', may be deployed on a proximal side of the tissue fold F such that its proximal collars of fused-anchor end 334' rests against or abuts the surface of the tissue, also as described above. Suture 38 may also pass from the tissue fold F and through the proximal hybrid anchor 310'.

Figure 23C:
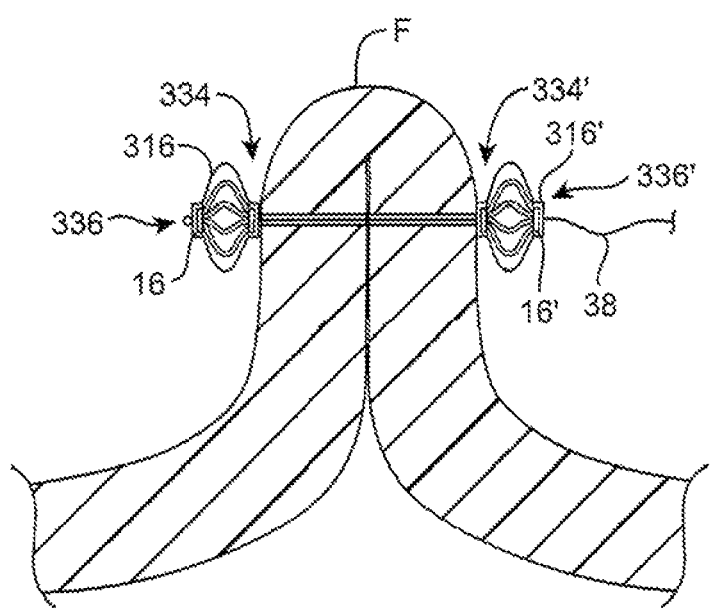

As the hybrid anchors 310, 310' are approximated towards one another by tensioning suture 38, the tissue is formed into a serosa-to-serosa contacting tissue fold F, as shown in FIG. 23C. As the hybrid anchors 310, 310" are further cinched towards one another, the free-floating collars 16, 16' of their respective free-anchor ends 336, 336' may freely move while the respective fused-anchor ends 334, 334' may each lie against the surface of tissue fold F. Thus, having the translating free-anchor ends 336, 336' of the apposed basket anchors positioned away from the plicated tissue while having the fused-anchor ends 334, 334' placed against the plicated tissue may ensure smooth anchor compression and cinching of the tissue.

In another variation, FIG. 24A illustrates a side view of another hybrid basket assembly 340 having a mesh anchor 312 with a basket anchor contained within having arm members or struts 342 which are formed in a curved, spiraled, or arcuate shape between collars 14, 16. When compressed for securing tissue, mesh anchor 312 may compress into its disk-shaped configuration, but curved or spiraled arm members 342 may compress into a looped, spiraled, or flower-shaped configuration, as shown in the top compressed view of FIG. 24B. Such a spiraled configuration may allow for compression of the basket anchor within the mesh anchor 312 while retaining a smooth or atraumatic outer diameter with respect to an inner surface of the mesh 318 when compressed.

In yet another variation, compressible anchor 350 may be comprised generally of a mesh 358, as described above, which is pre-formed to compress into a double-disk configuration. FIG. 25A shows a low-profile configuration of the anchor 350 having one or more radially-biased bulges 352 pre-formed between at least one inwardly-biased radius 354. When compressed, as shown in FIG. 25B, radially-biased bulges 352 may each flatten radially into a disk-shaped configuration adjacently formed with respect to one another while inwardly-biased radius 354 is biased to flatten in an opposite direction. As shown in the top compressed view in FIG. 25C, bulges 352 may essentially form hardened circumferential rings of flattened mesh 356 which further inhibit or prevent the tissue anchors from being pulled through the secured tissue. Although compressible anchor 350 is shown as a mesh basket, a basket anchor may also be placed therewithin, if so desired.

Figure 26A:
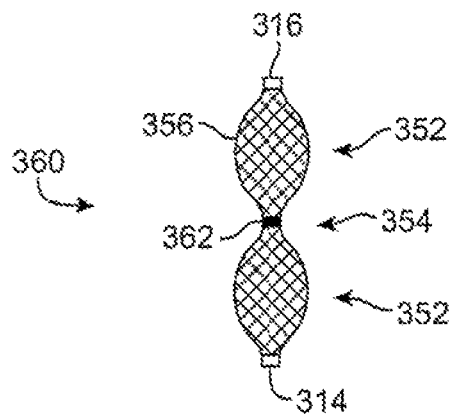
FIGS. 26A and 26B show the basket anchor of FIG. 25A having an additional ring, band, or other restraining structure integrated or otherwise attached to the mesh.
Figure 26B:
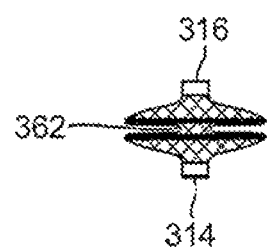

In a further variation, an additional ring, band, or other structure may be integrated with the anchor of FIGS. 25A to 25C to facilitate the formation of the circumferential rings when the anchor is flattened. For instance, FIGS. 26A and 26B show compressible anchor 360 having the ring, band, or other retaining structure 362 formed at or along inwardly-biased radius 354. This structure 362 may be integrally formed with mesh 356 by an adhesive or other mechanism. Structure 362 may be formed into, e.g., a circular or elliptical ring or band, made of any number of non-distensible or partially distensible polymeric or elastomeric materials, e.g., PTFE, silicon, urethane, etc., or any number of other metals or alloys, e.g., Nitinol, stainless steel, etc. When the anchor 360 expands from its low-profile configuration, as shown in FIG. 26A, the structure 362 may retain the portion of mesh 356 around radius 354 such that when the anchor 360 is flattened against the tissue surface, the bulges 352 may more easily flatten into their expanded configurations about radius 354, as shown in FIG. 26B.

Figure 27A:
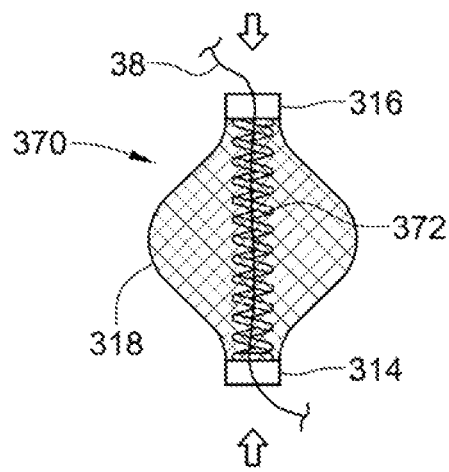
FIG. 27A to 27C show an anchor assembly in its low-profile configuration with a spring element connecting the collars of the anchor and a partially compressed anchor where the collars have been drawn or urged towards one another by the spring element, respectively.
Figure 27B:
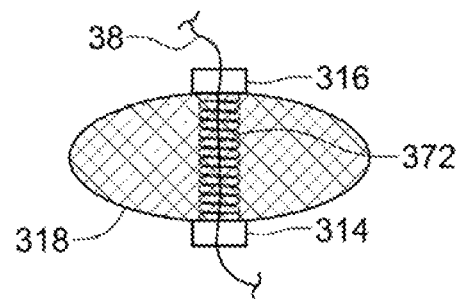
Figure 27C:
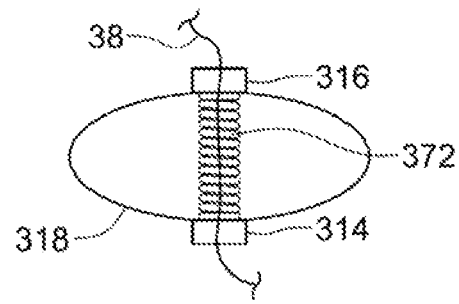

FIGS. 27A to 27C show yet another variation of the anchors which may include a biasing element therewithin to facilitate reconfiguration of the anchor from a low-profile deployment configuration to at least a partially expanded configuration. As illustrated in FIG. 27A, the anchor assembly 370 is configured as above with proximal 314 and distal 316 collars with mesh 318 connected between the two. A biasing element, such as a spring element 372, may be disposed within mesh 318 and connected to both collars 314, 316 at either end of spring element 372. Although shown as a spring in this example, the biasing element may alternatively be configured as various mechanisms such as an elastic band or element connected at either end to collars 314, 316. The spring element 372 is generally biased to urge collars 314, 316 towards one another, as indicated by the arrows in the figure, such that when anchor assembly 370 is free of the constraints of being contained within a needle body during delivery, collars 314, 316 are drawn towards one another to automatically urge mesh 318 into at least a partially reconfigured shape, as shown in FIG. 27B. FIG. 27C shows the anchor assembly of FIG. 27B with the mesh 318 partially removed only for clarity. As seen, collars 314, 316 have been drawn towards one another by spring element 372 such that mesh 318 has conformed at least partially info an expanded shape.

Spring element 372 may be a separate spring which is attached, e.g., via welding, adhesive, crimping, or other attachment mechanisms, etc., to collars 314, 318. However, in other alternatives, spring element 372 and collars 314, 316 may comprise an integral continuous structure. For instance, collars 314, 316 may be formed by winding the terminal ends of spring element 372 into closely wound coils or partial coils. Mesh 318 may be otherwise attached to the coil-formed collars 314, 316. Furthermore, spring element 372 may be made from a variety of metal, metal alloy, polymeric material, or combinations thereof. Examples of such metals and metal alloys may include, but are not limited to, stainless steel, nickel, titanium, nitinol, etc. while some examples of polymeric materials may include, but are not limited to, plastic, elastomers, polyurethane, salastic materials, etc.

Having spring element 372 urge the collars 314, 316 towards one another facilitates the complete expansion of the mesh 318 against a tissue surface when suture 38 is pulled or tensioned to draw the anchor against the tissue surface by inhibiting the anchor from inadvertently being pulled through a tissue surface. As spring element 372 is positioned through a central axis between collars 314, 316, suture 38 may be passed through the center of spring 372 such that anchor assembly 370 slides freely over suture 38. Alternatively, a terminal end of suture 38 may be secured against or attached to one of the collars 314, 316.

Figure 28A:
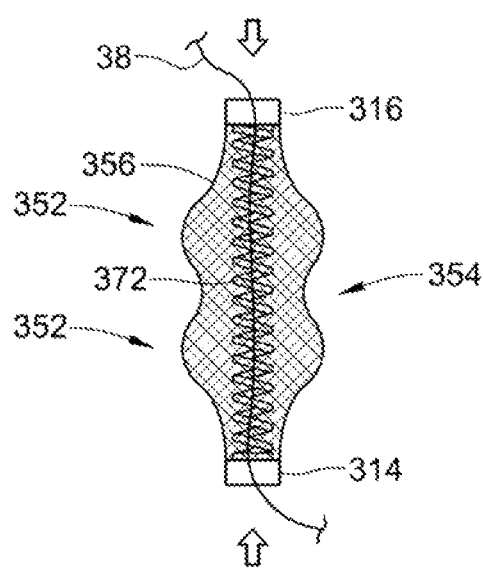
FIGS. 28A to 28C show the anchor of FIGS. 25A to 25C also including a spring element connecting the collars of the anchor.
Figure 28B:
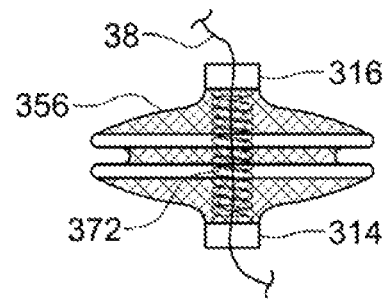
Figure 28C:
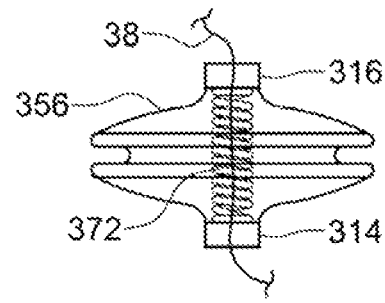

FIG. 28A illustrates the anchor assembly of FIGS. 25A to 25C with the addition of spring element 372 disposed within mesh 356 and attached at either end to collars 314, 316. As described above, mesh 356 of the compressible anchor may be pre-formed to compress into a double-disk configuration. The low-profile delivery configuration is shown in FIG. 28A as having one or more radially-biased bulges 352 pro-formed between at least one inwardly-biased radius 354. With spring element 372 disposed within mesh 356 and attached to collars 314, 316, the anchor may be urged to reconfigure itself into at least a partially expanded and compressed configuration where the radially-biased bulges 352 may each partially flatten radially into a disk-shaped configuration adjacently formed with respect to one another while inwardly-biased radius 354 is biased to at least partially flatten in the opposite direction, as shown in FIG. 28B. FIG. 28C shows the anchor assembly of FIG. 28B with the mesh 356 partially removed only for clarity. As seen, collars 314, 316 have been drawn towards one another by spring element 372 such that mesh 356 has conformed at least partially into its double-disk configuration. Suture 38 may also be seen as being slidably disposed through spring element 372. As above, spring element 372 may comprise a separate biased element which is attached or connected between the collars 314, 316. Alternatively, collars 314, 316 may also be formed by winding the terminal ends of spring element 372 into closely wound coils or partial coils to form a continuous structure.

Although spring elements 372 are shown as partially approximating the collars 314, 316 toward one another to result in a partially expanded mesh 356, spring elements 372 having a relatively higher spring force may alternatively be used. Use of a spring element having a high spring force may result in an anchor where once such an anchor is unconstrained, the collars 314, 316 may be drawn as closely together as practicable by the spring element 372 such that mesh 356 is fully reconfigured into a completely expanded configuration.

Figure 29:
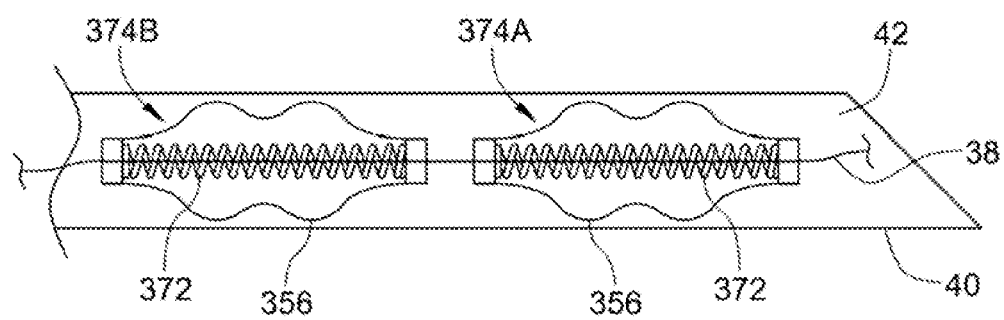
FIG. 29 shows a partial cross-sectional view of the anchors of FIGS. 28A to 28C disposed within a needle lumen.

FIG. 29 illustrates the anchor of FIG. 28 in its low-profile delivery configuration disposed within needle lumen 42 of delivery needle 40. As shown, a first mesh anchor 374A is positioned within needle lumen 42 distally of second mesh anchor 374B. Each anchor 374A, 374B is shown in cross-section with mesh 356 partially removed for clarity to illustrate spring elements 372 disposed within each respective anchor 374A, 374B attached to both collars. When anchor 374A, 374B are constrained in their low-profile configuration, spring elements 372 may be under tension and are biased to pull or draw their respective collars towards one another. Suture 38 may be seen passing through each respective spring element 372 through each anchor 374A, 374B.

Figure 30A:
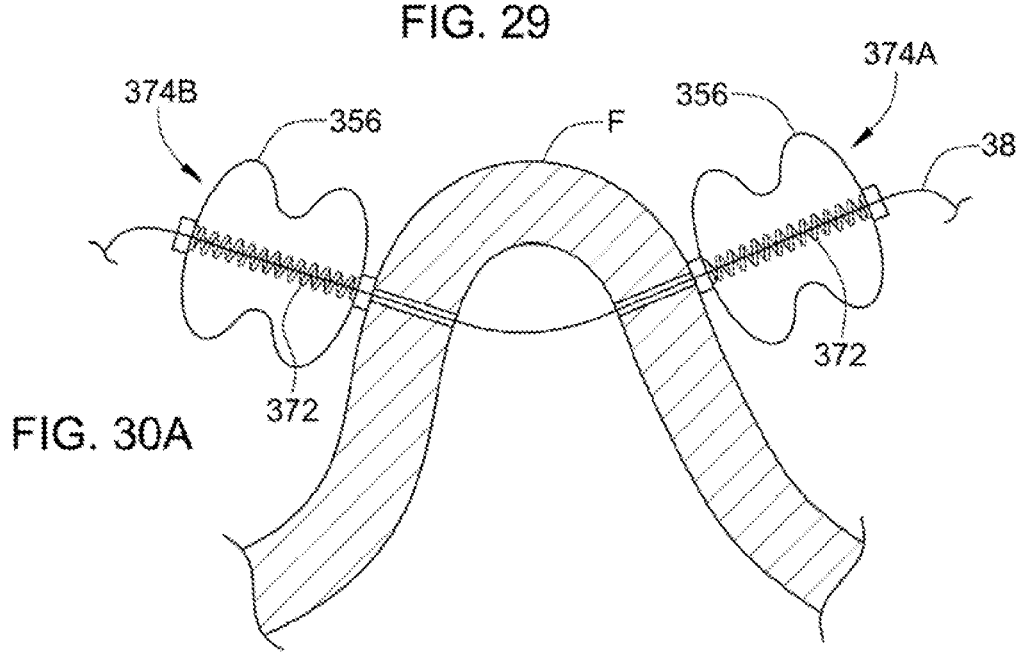
FIGS. 30A and 30B illustrate anchors which are partially expanded by the spring elements prior to being approximated towards one another to secure a tissue fold.

After first anchor 374A is ejected from needle 40 on a first respective side of tissue fold F, second anchor 374B may be ejected from needle 40 on a second respective side of tissue fold F in one example of securing a tissue fold F, as shown in FIG. 30A and as described above. As shown, once anchors 374A, 374B have been deployed and are free from the constraints of being contained within needle lumen 42, the collars are free to move towards one another under the force of spring elements 372 over suture 38. The resulting configuration of the mesh 356 may be seen as being at least partially expanded under the biased spring force from spring elements 372. Moreover, because of the biasing force from the elastic element or spring element 372, the mesh 356 is urged to reconfigure itself into its partially expanded shape. Accordingly, as the anchors 374A, 374B are pushed distally through needle lumen 42, the anchors 374A, 374B themselves facilitate automatic reconfiguration into a "popped-open" shape.

Figure 30B:
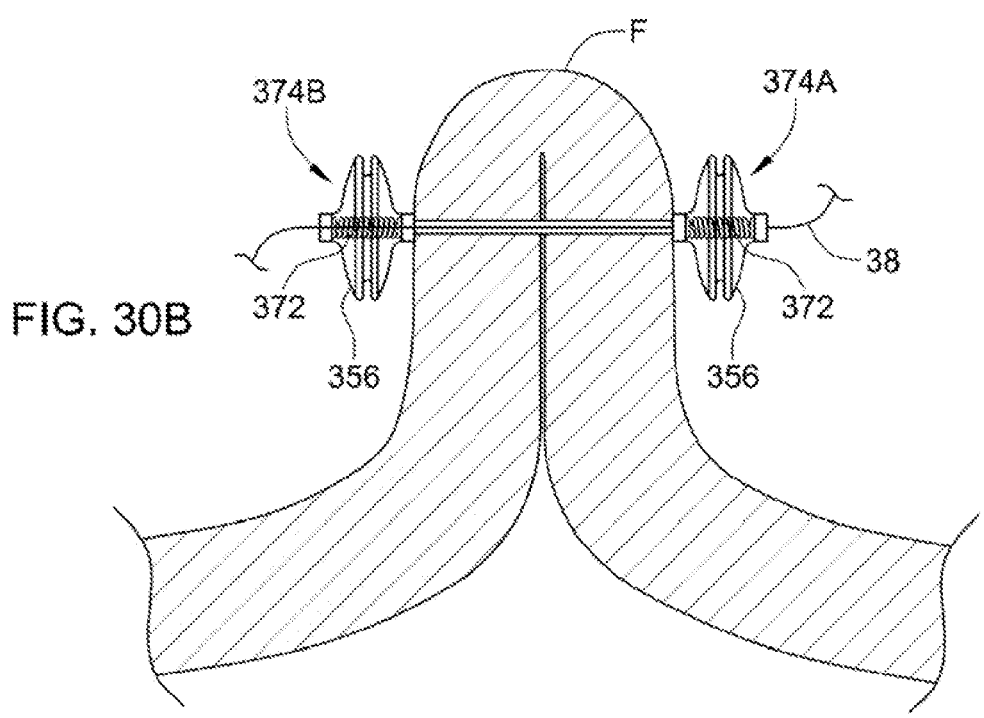

With anchor 374A, 374B at least partially expanded, when suture 38 is pulled or tensioned to draw anchors 374A, 374B towards one another to secure tissue fold F into its plicated configuration, the anchors 374A, 374B are inhibited from collapsing back into their low-profile configuration by spring elements 372 and being pulled through the tissue fold F. Rather, because anchors 374A, 374B are already partially expanded, when suture 38 is tensioned, anchors 374A, 374B may naturally assume their fully expanded configuration against the tissue fold F, further inhibiting anchors 374A, 374B from being pulled through, as shown in FIG. 30B.

Although the examples above illustrate anchors 374A, 374B used to secure a single tissue fold F, the anchor assemblies described above may be utilized in any number of procedures and in various regions of the body. For instance, anchors 374A, 374B may be used not only to hold tissue folds but also to join one or more tissue layers, or also to approximate one or more tissue edges and tissue openings which may have been created surgically or otherwise present naturally in the patient body.

Although a number of illustrative variations are described above, it will be apparent to those skilled in the art that various changes and modifications may be made thereto without departing from the scope of the invention. Any of the modifications to an anchor, e.g., number of arms, arm configuration, cross-sectional variations, anchor collar length, coatings or coverings over the anchor, etc., may be done in a variety of combinations with one another. For instance, depending upon the desired loading characteristics, an anchor may be made having a number of arms with various cross-sectional areas along one or more of the arm lengths and may additionally have one or both collars varied in length.

Any of the combinations or modifications is intended to be within the scope of this invention. Moreover, although configurations may be shown with various types of anchors, it is intended that the various configurations be utilized in various combinations as practicable, it is intended in the appended claims to cover all such changes and modifications that fall within the true spirit and scope of the invention.

The invention claimed is:
1. A tissue anchor system, comprising:
an anchor delivery device;
a first tissue anchor in the anchor delivery device comprising a first mesh supported by a first resilient frame;
a first collar attached to the first resilient frame;
a second tissue anchor in the anchor delivery device comprising a second mesh supported by a second resilient frame;
a second collar attached to the second resilient frame;
a suture extending through or attached to the first tissue anchor and the second tissue anchor; and
a cinch moveable on the suture towards the second collar;
with the first and second tissue anchors resiliently expandable from a collapsed position when in the delivery device, to an expanded position when moved out of the delivery device for engaging a tissue surface at a surgical site, and with the second tissue anchor separate from the first tissue anchor.

2. The tissue anchor system of claim 1 wherein the first and second tissue anchors are linked together only via a single suture.

3. The tissue anchor system of claim 1 wherein the first and second resilient frames each comprise a spring of a material selected from the group consisting of stainless steel, nickel, titanium, nitinol, plastic, elastomers, polyurethane, and salastic materials.

4. The tissue anchor system of claim 1 wherein the first and second mesh surround the first and second frames, respectively.

5. The tissue anchor system of claim 1 with the first and second frames floating freely within the first and second meshes, respectively.

6. The tissue anchor system of claim 1 with the suture passing freely through the first and second anchors.

7. A tissue anchor system, comprising:
an anchor delivery device;
a first tissue anchor in the anchor delivery device comprising a first mesh pouch supported by a first resilient frame;
a first collar attached to the first resilient frame;
a second tissue anchor in the anchor delivery device comprising a second mesh pouch supported by a second resilient frame;
a second collar attached to the second resilient frame;
with the first and second tissue anchors unconnected to each other except for a suture extending through or attached to the first tissue anchor and the second tissue anchor;
a cinch moveable on the suture in only one direction; and
with the first and second tissue anchors resiliently expandable from a collapsed position when in the delivery device, to an expanded position when moved out of the delivery device for engaging a tissue surface at a surgical site.

8. The tissue anchor system of claim 7 wherein the first and second resilient frames each comprise a spring.

9. The tissue anchor system of claim 7 wherein the spring comprises a material selected from the group consisting of stainless steel, nickel, titanium, nitinol, plastic, elastomers, polyurethane, and salastic materials.

10. The tissue anchor system of claim 7 wherein the cinch is adapted to slide uni-directionally along the suture.

11. The tissue anchor system of claim 7 wherein the first and second mesh pouches surround the first and second frames, respectively.

12. The tissue anchor system of claim 7 with the first and second frames floating freely within the first and second mesh pouches, respectively.

13. The tissue anchor system of claim 7 with the suture passing freely through the first and second anchors.

14. Tissue anchor apparatus, comprising:
an anchor delivery device including a hollow needle;
a first tissue anchor in the hollow needle comprising a first mesh material supported by a first frame,
a second tissue anchor in the hollow needle comprising a second mesh material supported by a second frame,
a suture extending through or attached to the first tissue anchor and the second tissue anchor, with the second tissue anchor slidable along the suture toward the first collar;
with the first and second tissue anchors resiliently expandable from a collapsed position when in the hollow needle, to an expanded position when moved out of the hollow needle for engaging a tissue surface at a surgical site.

15. The apparatus of claim 14 with the first tissue anchor further comprising a first distal collar attached to a distal end of the first resilient frame and a first proximal collar attached to a proximal end of the first resilient frame; and
with the second tissue anchor further including a second distal collar attached to a distal end of the second resilient frame and a second proximal collar attached to a proximal end of the second resilient frame; and
with the first proximal collar and the second distal collar comprising separate components.

16. The apparatus of claim 14 wherein the first and second mesh materials surround the first and second frames, respectively.

17. The apparatus of claim 14 with the first and second frames floating freely within the first and second mesh materials, respectively.

18. The apparatus of claim 14 with the suture passing freely through the first and second anchors.

19. The apparatus of claim 14 with the first and second tissue anchors linked together only via the suture.

* * * * *